(12) United States Patent
Mantri et al.

(10) Patent No.: US 11,877,818 B2
(45) Date of Patent: Jan. 23, 2024

(54) INTEGRATION OF ROBOTIC ARMS WITH SURGICAL PROBES

(71) Applicant: PROCEPT BioRobotics Corporation, Redwood City, CA (US)

(72) Inventors: Surag Mantri, East Palo Alto, CA (US); Kevin Patrick Staid, Lowell, MA (US); David Vincent Adams, Redwood City, CA (US); Jason Hemphill, Los Gatos, CA (US); Jonathan Trung Hoang, Redwood City, CA (US); Rishabh Mayur Sirdesai, Menlo Park, CA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 0 days.

(21) Appl. No.: 16/940,085

(22) Filed: Jul. 27, 2020

(65) Prior Publication Data

US 2021/0401522 A1 Dec. 30, 2021

Related U.S. Application Data

(60) Provisional application No. 63/044,914, filed on Jun. 26, 2020.

(51) Int. Cl.
*A61B 34/00* (2016.01)
*B25J 9/10* (2006.01)
(Continued)

(52) U.S. Cl.
CPC .......... *A61B 34/71* (2016.02); *A61B 1/00149* (2013.01); *A61B 8/12* (2013.01);
(Continued)

(58) Field of Classification Search
CPC ......... A61B 34/71; A61B 8/4218; A61B 8/12; A61B 34/30; A61B 2034/301–306;
(Continued)

(56) References Cited

U.S. PATENT DOCUMENTS

| 4,561,798 A | 12/1985 | Elcrin |
| 4,932,956 A | 6/1990 | Reddy |

(Continued)

FOREIGN PATENT DOCUMENTS

| CN | 105764436 A | 7/2016 |
| CN | 111449694 | 7/2020 |

(Continued)

OTHER PUBLICATIONS

Lim et al. "Robotic Transrectal Ultrasound-Guided Prostate Biopsy." IEEE Trans BME. Jan. 7, 2019. 11 pages. (Year: 2019).*

(Continued)

*Primary Examiner* — Angela M Hoffa
(74) *Attorney, Agent, or Firm* — FISHERBROYLES, LLP; John K. Shimmick

(57) ABSTRACT

Embodiments of the present disclosure provide improved methods and apparatus for coupling a probe to an instrument device manipulator (e.g., robotic arm). In some embodiments, a probe, which may be carried by a handpiece, is configured to couple to the end of a device manipulator of a robotic arm. A transmission can be provided that is configured to couple to the probe and also couple to the instrument device manipulator. The transmission can be configured to receive motion input from the instrument device manipulator and transfer the motion input into motion of the probe. The transmission can provide improved movement of the probe. By decreasing the number of components on the handpiece and probe, the handpiece and (Continued)

probe can be provided as a sterile, single use consumable device and the transmission can be reused.

21 Claims, 25 Drawing Sheets

(51) Int. Cl.
| | | |
|---|---|---|
| *B25J 15/04* | (2006.01) | |
| *A61B 1/00* | (2006.01) | |
| *A61B 8/12* | (2006.01) | |
| *A61B 8/00* | (2006.01) | |
| *A61B 10/04* | (2006.01) | |
| *A61B 34/30* | (2016.01) | |
| *A61B 1/307* | (2006.01) | |
| *A61B 34/20* | (2016.01) | |

(52) U.S. Cl.
CPC ............ *A61B 8/4218* (2013.01); *A61B 10/04* (2013.01); *B25J 9/102* (2013.01); *B25J 15/0441* (2013.01); *A61B 1/307* (2013.01); *A61B 2034/2059* (2016.02); *A61B 2034/301* (2016.02)

(58) Field of Classification Search
CPC ................ A61B 34/32–37; B25J 9/102; B25J 9/10–1045; B25J 15/04–0458
See application file for complete search history.

(56) References Cited

U.S. PATENT DOCUMENTS

| | | | |
|---|---|---|---|
| 6,039,695 A | 3/2000 | Sakamoto | |
| 6,331,181 B1 | 12/2001 | Tierney | |
| 6,338,714 B1 | 1/2002 | Krause | |
| 7,021,173 B2 * | 4/2006 | Stoianovici | B25J 9/06 |
| | | | 74/490.03 |
| 7,882,841 B2 | 2/2011 | Aljuri | |
| 8,152,816 B2 | 4/2012 | Tuma | |
| 8,229,188 B2 | 7/2012 | Rusko | |
| 8,398,541 B2 | 3/2013 | Dimaio | |
| 8,660,635 B2 | 2/2014 | Simon | |
| 8,814,921 B2 | 8/2014 | Aljuri | |
| 8,827,948 B2 * | 9/2014 | Romo | A61B 34/35 |
| | | | 604/95.04 |
| 8,961,533 B2 * | 2/2015 | Stahler | A61B 8/12 |
| | | | 606/108 |
| 9,072,452 B2 | 7/2015 | Vayser | |
| 9,144,461 B2 | 9/2015 | Kruecker | |
| 9,277,969 B2 | 3/2016 | Brannan | |
| 9,314,306 B2 * | 4/2016 | Yu | A61B 8/12 |
| 9,364,251 B2 | 6/2016 | Aljuri | |
| 9,610,131 B2 * | 4/2017 | Stoianovici | A61B 34/70 |
| 9,737,371 B2 | 8/2017 | Romo | |
| 9,867,635 B2 | 1/2018 | Alvarez | |
| 9,877,788 B2 * | 1/2018 | Stoianovici | A61B 10/04 |
| 10,130,427 B2 * | 11/2018 | Tanner | A61B 34/30 |
| 10,226,298 B2 | 3/2019 | Ourselin | |
| 10,231,867 B2 | 3/2019 | Alvarez | |
| 10,307,214 B2 * | 6/2019 | Lathrop | A61B 34/37 |
| 10,423,757 B2 | 9/2019 | Kruecker | |
| 10,441,371 B2 * | 10/2019 | Hendrick | A61B 17/00234 |
| 10,448,956 B2 | 10/2019 | Gordon | |
| 10,555,780 B2 * | 2/2020 | Tanner | A61B 34/20 |
| 10,555,785 B2 * | 2/2020 | Yeung | A61B 90/30 |
| 10,646,295 B2 * | 5/2020 | Stoianovici | A61B 34/30 |
| 10,779,897 B2 * | 9/2020 | Rockrohr | A61B 34/30 |
| 11,071,601 B2 | 7/2021 | Staid | |
| 11,096,753 B1 | 8/2021 | Mantri | |
| 11,278,451 B2 | 3/2022 | Andrews | |
| 11,357,586 B2 | 6/2022 | Huang | |
| 11,590,319 B2 * | 2/2023 | DeBuys | A61B 8/445 |
| 2002/0121577 A1 | 9/2002 | Metelski | |
| 2004/0024311 A1 | 2/2004 | Quaid | |
| 2004/0034282 A1 | 2/2004 | Quaid | |
| 2006/0142657 A1 | 6/2006 | Quaid | |
| 2006/0205996 A1 | 9/2006 | Presthus | |
| 2008/0027420 A1 | 1/2008 | Wang | |
| 2009/0306692 A1 | 12/2009 | Barrington | |
| 2010/0036245 A1 | 2/2010 | Yu | |
| 2012/0035462 A1 | 2/2012 | Maurer, Jr. | |
| 2012/0071894 A1 * | 3/2012 | Tanner | A61B 34/35 |
| | | | 606/130 |
| 2013/0218186 A1 | 8/2013 | Dubois | |
| 2013/0239392 A1 | 9/2013 | Solomon | |
| 2014/0039314 A1 | 2/2014 | Dan | |
| 2014/0094968 A1 | 4/2014 | Taylor | |
| 2014/0142438 A1 | 5/2014 | Ludwin | |
| 2014/0194896 A1 | 7/2014 | Frimer | |
| 2014/0309649 A1 | 10/2014 | Alvarez | |
| 2015/0025539 A1 | 1/2015 | Alvarez | |
| 2015/0080907 A1 | 3/2015 | Herrell | |
| 2015/0088107 A1 | 3/2015 | Aljuri | |
| 2015/0173726 A1 | 6/2015 | Lohmeier | |
| 2015/0366546 A1 | 12/2015 | Kamen | |
| 2016/0067450 A1 | 3/2016 | Kowshik | |
| 2016/0262827 A1 | 9/2016 | Ross | |
| 2017/0014269 A1 | 1/2017 | Draheim | |
| 2017/0020253 A1 | 1/2017 | Drozdowicz | |
| 2017/0189127 A1 | 7/2017 | Weir | |
| 2017/0202537 A1 | 7/2017 | Ippolito | |
| 2017/0245878 A1 | 8/2017 | Aljuri | |
| 2017/0245949 A1 * | 8/2017 | Randle | B25J 17/0291 |
| 2017/0273797 A1 | 9/2017 | Gordon | |
| 2018/0014891 A1 | 1/2018 | Krebs | |
| 2018/0021960 A1 * | 1/2018 | Grant | B25J 17/0283 |
| | | | 74/490.06 |
| 2018/0028261 A1 | 2/2018 | Chen | |
| 2018/0263647 A1 | 9/2018 | Aljuri | |
| 2018/0263685 A1 | 9/2018 | Onik | |
| 2018/0318011 A1 | 11/2018 | Leibinger | |
| 2018/0353253 A1 | 12/2018 | Bowling | |
| 2019/0015166 A1 | 1/2019 | Mahoney | |
| 2019/0021753 A1 | 1/2019 | Jinno | |
| 2019/0076674 A1 | 3/2019 | Ergün | |
| 2019/0105023 A1 | 4/2019 | Aljuri | |
| 2019/0105117 A1 | 4/2019 | Brisson | |
| 2019/0142396 A1 * | 5/2019 | Stoianovici | B25J 9/003 |
| | | | 600/567 |
| 2019/0201214 A1 | 7/2019 | Miller | |
| 2019/0202066 A1 | 7/2019 | Maret | |
| 2019/0231450 A1 | 8/2019 | Waterbury | |
| 2019/0262057 A1 | 8/2019 | Grant | |
| 2019/0321119 A1 * | 10/2019 | Yeung | A61B 90/50 |
| 2019/0336238 A1 | 11/2019 | Yu | |
| 2020/0008874 A1 | 1/2020 | Barbagli | |
| 2020/0020249 A1 | 1/2020 | Jarc | |
| 2020/0138454 A1 | 5/2020 | Patel | |
| 2020/0261297 A1 | 8/2020 | Strydom | |
| 2020/0360097 A1 | 11/2020 | Dimaio | |
| 2020/0360100 A1 * | 11/2020 | Mantri | A61B 90/37 |
| 2020/0405403 A1 * | 12/2020 | Shelton, IV | A61B 46/10 |
| 2021/0030496 A1 | 2/2021 | Devengenzo | |
| 2021/0137612 A1 | 5/2021 | Staid | |
| 2021/0378766 A1 | 12/2021 | Staid | |
| 2021/0401521 A1 | 12/2021 | Mantri | |
| 2022/0273166 A1 * | 9/2022 | Nord | A61B 1/00133 |

FOREIGN PATENT DOCUMENTS

| | | |
|---|---|---|
| EP | 1486900 | 12/2004 |
| NL | 1019547 | 5/2003 |
| WO | 2008083407 | 7/2008 |
| WO | 2009111736 | 9/2009 |
| WO | 2011097505 | 8/2011 |
| WO | 2013053614 | 4/2013 |
| WO | 2013130895 | 9/2013 |
| WO | 2014127242 | 8/2014 |
| WO | 2014165703 | 10/2014 |
| WO | 2015035249 | 3/2015 |
| WO | 2015200538 | 12/2015 |
| WO | 2016004071 | 1/2016 |
| WO | 2016037132 | 3/2016 |

(56) References Cited

FOREIGN PATENT DOCUMENTS

| WO | 2016037137   | 3/2016  |
|----|--------------|---------|
| WO | 2016054256   | 4/2016  |
| WO | 2017161331   | 9/2017  |
| WO | 20170192603  | 9/2017  |
| WO | 2018013848   | 1/2018  |
| WO | 2019032986   | 2/2019  |
| WO | 2019137665   | 7/2019  |
| WO | 2019246580   | 12/2019 |
| WO | 2020180724   | 9/2020  |
| WO | 2020181278   | 9/2020  |
| WO | 2020181280   | 9/2020  |
| WO | 2020181281   | 9/2020  |
| WO | 2020181290   | 9/2020  |
| WO | 2021130229   | 7/2021  |

OTHER PUBLICATIONS

Stoianovici et al. "MRI-Safe Robot for Endorectal Prostate Biopsy." IEEE/ASME Trans Mechatronics, vol. 19, No. Aug. 4, 2014. pp. 1289-1299. (Year: 2014).*
Office Action (final) for U.S. Appl. No. 16/939,880, 7 pages (dated Mar. 8, 2021).
Office Action (final) for U.S. Appl. No. 16/939,972, 13 pages (dated Jan. 8, 2021).
Office Action (final) for U.S. Appl. No. 16/940,100, 12 pages (dated Mar. 23, 2021).
Response to Non-Final Office Action for U.S. Appl. No. 16/939,880, 9 pages (dated Mar. 1, 2021).
Response to Non-Final Office Action for U.S. Appl. No. 16/940,100, 8 pages (dated Mar. 11, 2021).
Christoforou et al., Robotic Arm for Magnetic Resonance Imaging Guided Interventions, 2006, IEEE, p. 1-6 (Year: 2006).
Dwyer et al., A miniaturised robotic probe for real-time intraoperative fusion of ultrasound and endomicroscopy, 2015, IEEE, pg. ( Year: 2015).
International Search Report and Written Opinion for PCT/US2020/058884, 11 pages (dated Feb. 1, 2021).
Marmol et al., ArthroSLAM: Multi-Sensor Robust Visual Localization for Minimally Invasive Orthopedic Surgery, 2018, IEEE, p. 3882-3889 (Year: 2018).
Rosa et al., Laparoscopic optical biopsies: In vivo robotized mosaicing with probe-based confocal endomicroscopy, 2011, IEEE, p. 1339-1345 (Year: 2011).
Office Action (Final) for U.S. Appl. No. 16/940,100, 15 pages (dated May 4, 2022).
Response to Non-Final Office Action for U.S. Appl. No. 16/940,100, 11 pages (dated Apr. 20, 2022).
Notice of Allowance for U.S. Appl. No. 16/939,880, 8 pages (dated Jun. 2, 2021).
Notice of Allowance for U.S. Appl. No. 16/939,972, 12 pages (dated May 13, 2021).
International Search Report and Written Opinion for International Application No. PCT/US2021/070760, 20 pages (dated Sep. 28, 2021).
Notice of Allowance for U.S. Appl. No. 17/304,572, 8 pages (dated Feb. 27, 2023).
Office Action (Non-Final) for U.S. Appl. No. 16/940,100, 12 pages (dated Dec. 7, 2020).
Office Action (Non-Final) for U.S. Appl. No. 16/940,100, 13 pages (dated Dec. 20, 2021).
Office Action (Non-Final) for U.S. Appl. No. 16/940,100, 16 pages (dated Feb. 23, 2023).
Office Action (Non-Final) for U.S. Appl. No. 17/304,572, 8 pages (dated Nov. 29, 2022).
Chirstoforou et al., Manipulator for magnetic resonance imaging guided interventions: design, prototype and feasibility, 2006, IEEE p. 3838-3843 (Year: 2006).
Kiao et al., Ultrasound Guided Robotic System for Transperineal Biopsy of the Prostate, 2006, IEEE, p. 1315-1320 (Year: 2006).
Jakopec et al., Acrobot: a "hands-on" robot for total knee replacement surgery, 2002, IEEE, p. 116-120 (Year: 2002).
Notice of Allowance for U.S. Appl. No. 17/304,572, 9 pages (dated Jun. 5, 2023).
Sen et al., A cooperatively controlled robot for ultrasound monitoring of radiation therapy, 2013, IEEE, p. 3071-3076 (Year: 2013).

* cited by examiner

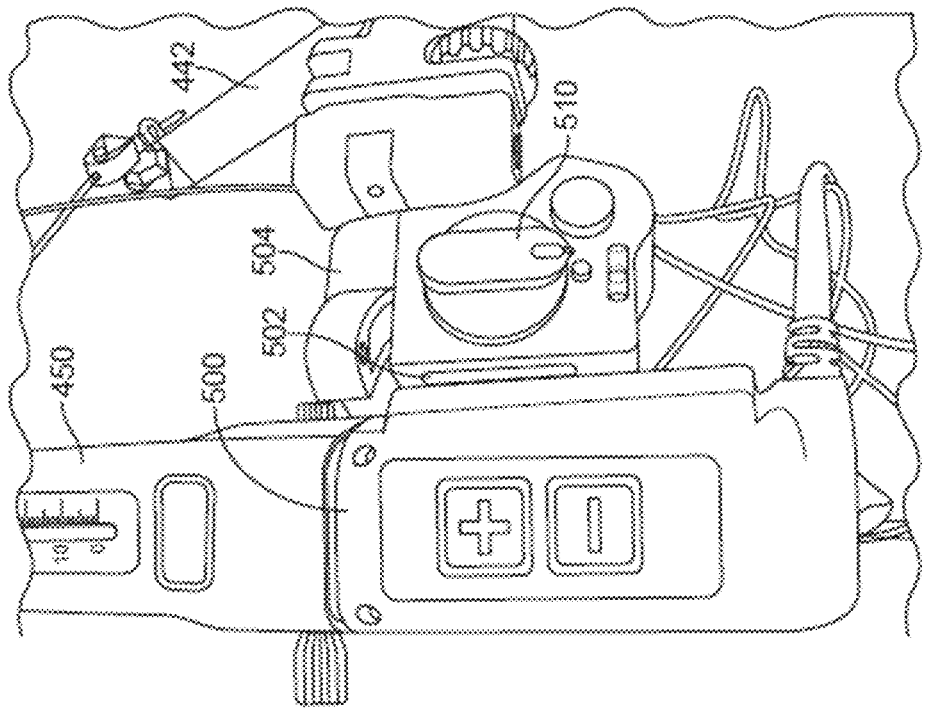
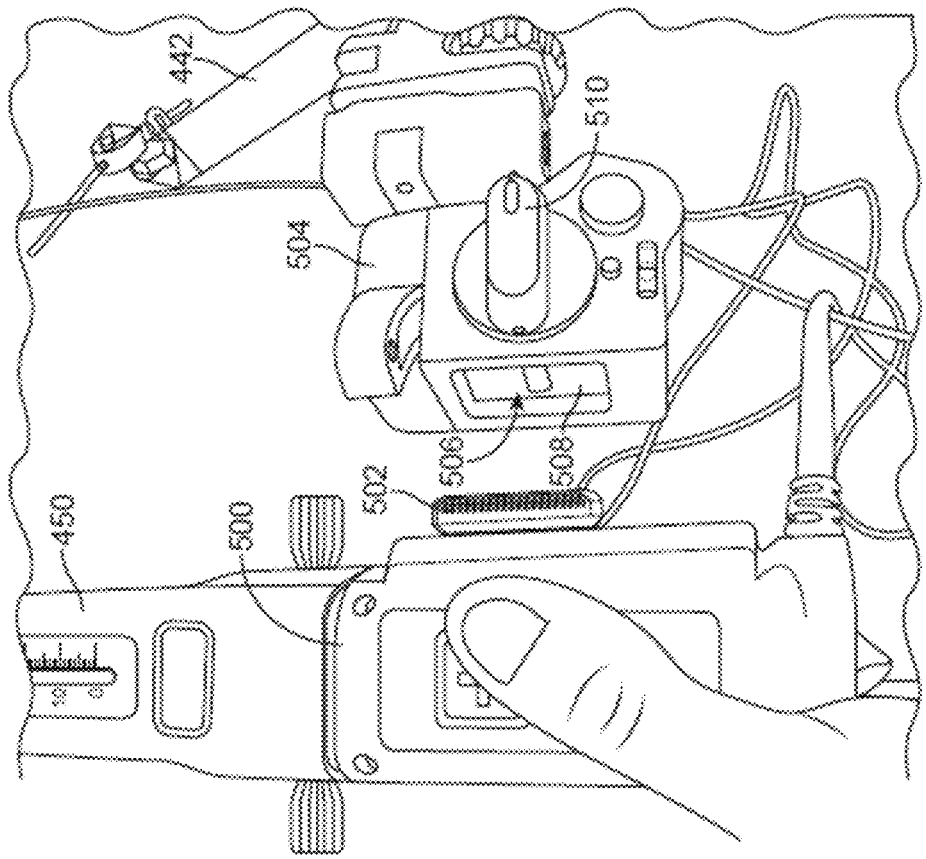
FIG. 5B
FIG. 5A

INTEGRATION OF ROBOTIC ARMS WITH SURGICAL PROBES

RELATED APPLICATIONS

This application claims the benefit under 35 U.S.C. § 119(e) of U.S. Provisional Application No. 63/044,914, filed Jun. 26, 2020, the disclosure of which is hereby incorporated, in its entirety, by this reference.

The subject matter of this application is related to International Application No. PCT/US2015/048695, filed Sep. 4, 2015, published as WO 2016/037137 on Mar. 10, 2016, and International Application No. PCT/US2020/021756, filed Mar. 9, 2020, published as WO 2020/181290 on Sep. 10, 2020, entitled ROBOTIC ARMS AND METHODS FOR TISSUE RESECTION AND IMAGING, the entire contents of which applications are incorporated herein by reference.

BACKGROUND

The field of the present disclosure is related to the treatment of tissue with energy, and more specifically to the surgical implements used in such treatments. Prior approaches of conducting such treatments utilize one or more instruments that may be manually controlled, or in some cases, attached to an instrument device manipulator, such as a robotic arm.

Work in relation to the present disclosure suggest that at least some of the prior treatment devices are less than ideally suited for coupling with a robotic arm. Robotic arms used in surgical systems typically have motors on the end of the arm. Because these motors are on the end of the arm, their size and performance characteristics is somewhat limited. Also, at least some of the prior surgical instruments are not well suited for placement on a robotic arm. For example, at least some of the prior instruments may have performance requirements that are not readily met with prior robotic arms.

In light of the above, there is a need for instruments that can be readily coupled to a robotic arm and provide improved performance.

At least some of these shortcomings will be ameliorated with the present disclosure.

SUMMARY

Embodiments of the present disclosure provide improved methods and apparatus for coupling a probe to an instrument device manipulator (e.g., robotic arm). In some embodiments, a probe, which may be carried by a handpiece, is configured to couple to the end of a device manipulator of a robotic arm. A transmission can be provided that is configured to couple to the probe and also couple to the instrument device manipulator. The transmission can be configured to receive motion input from the instrument device manipulator and transfer the motion input into motion of the probe. The transmission can provide improved movement of the probe. In some embodiments, the transmission may cause the probe to move linearly, rotationally, and may cause the probe to oscillate according to a predetermined treatment plan. In some embodiments, the transmission is configured to be reused and the handpiece and treatment probe are configured as a consumable. By decreasing the number of components on the handpiece and probe, the handpiece and probe can be provided as a sterile, single use consumable device and the transmission reused.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIGS. 5A and 5B show top views of a coupling between a treatment probe and a first robotic arm, in accordance with some embodiments, with FIG. 5A showing the treatment probe and the first robotic arm uncoupled and FIG. 5B showing the treatment probe and the first robotic arm coupled;

Figure 8:
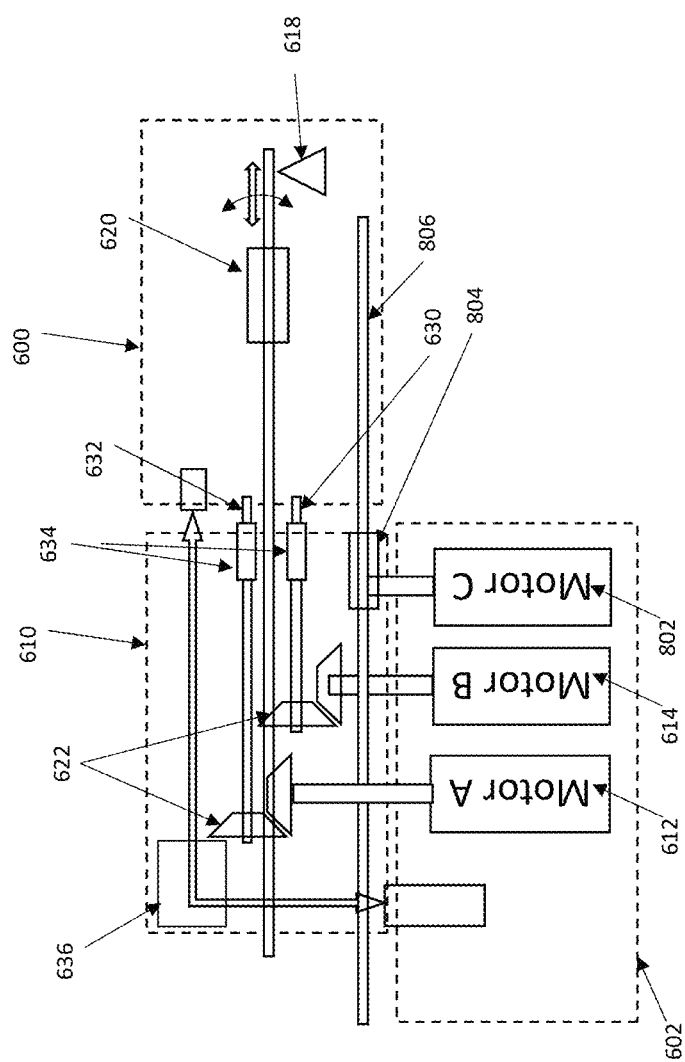
Figure 9:
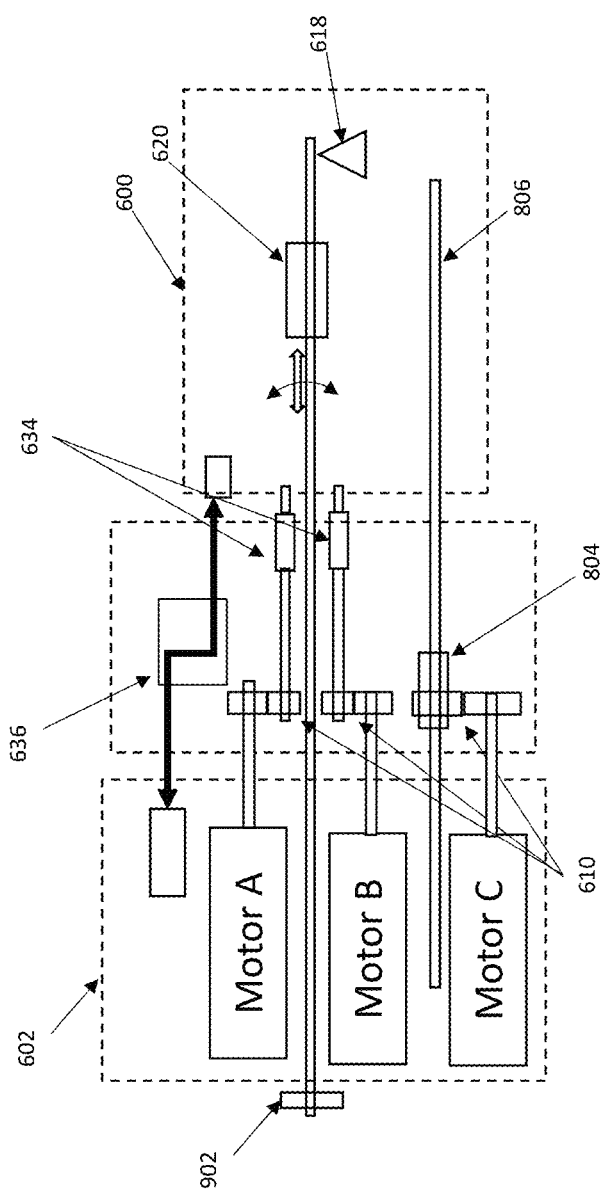
Figure 10:
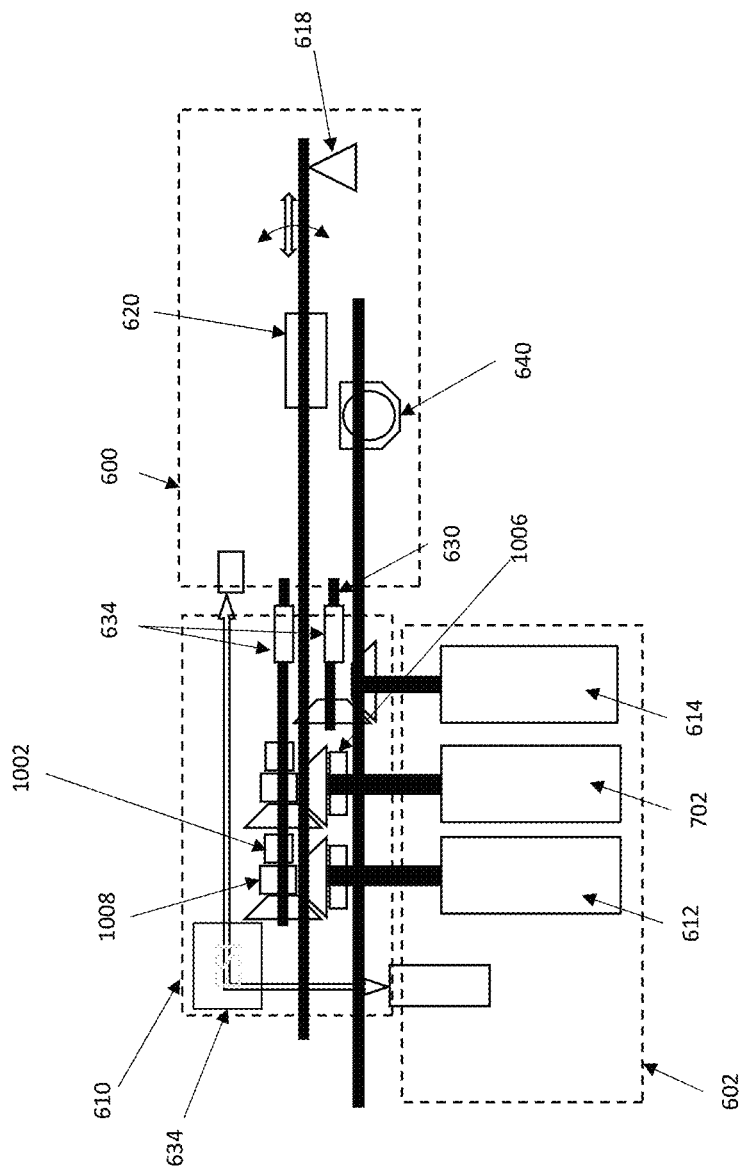
Figure 11:
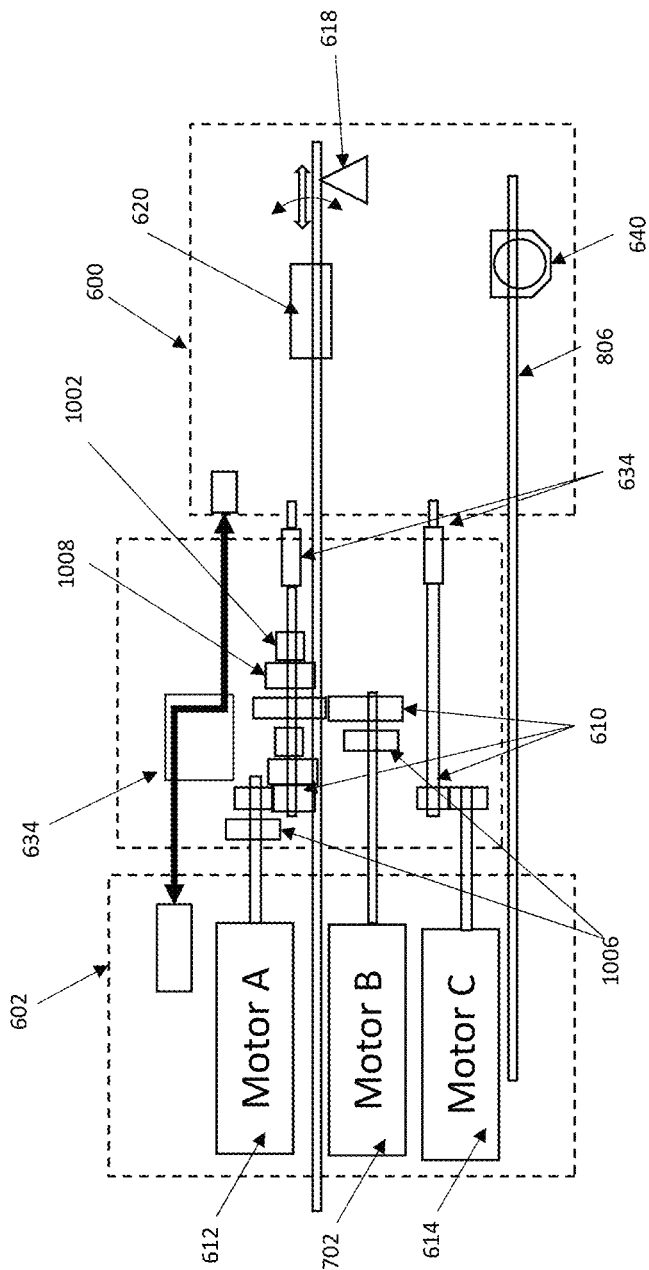
Figure 12:
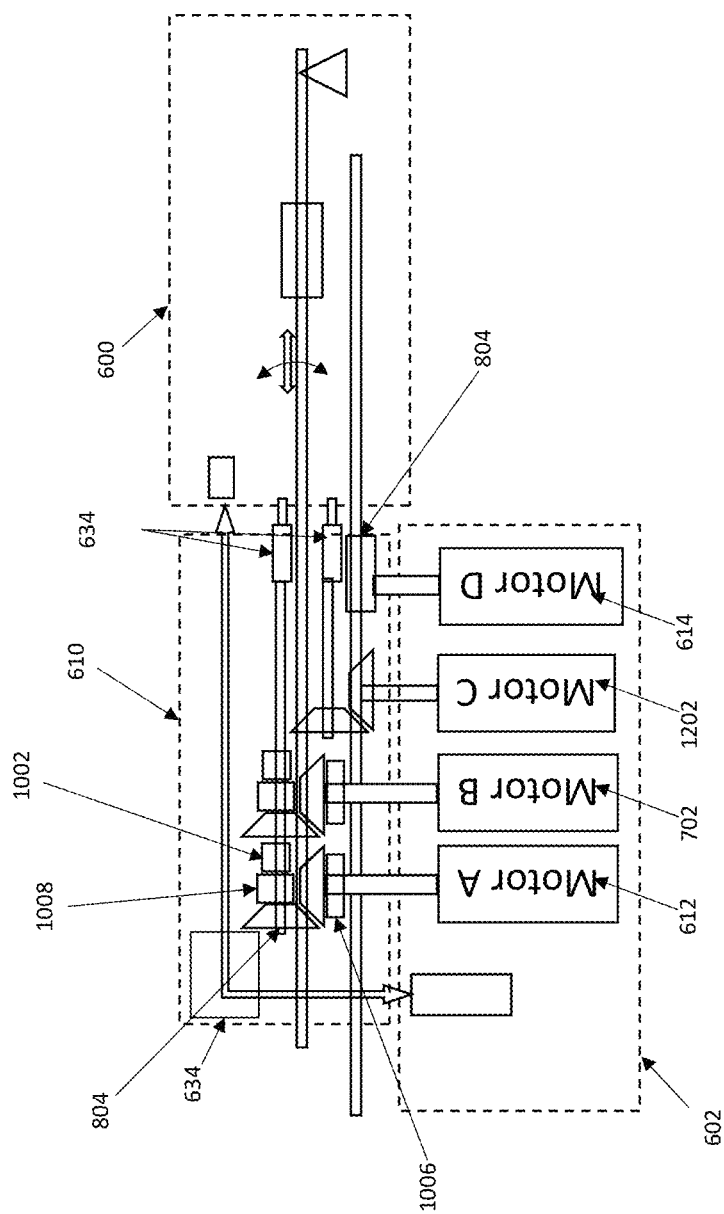
Figure 13:
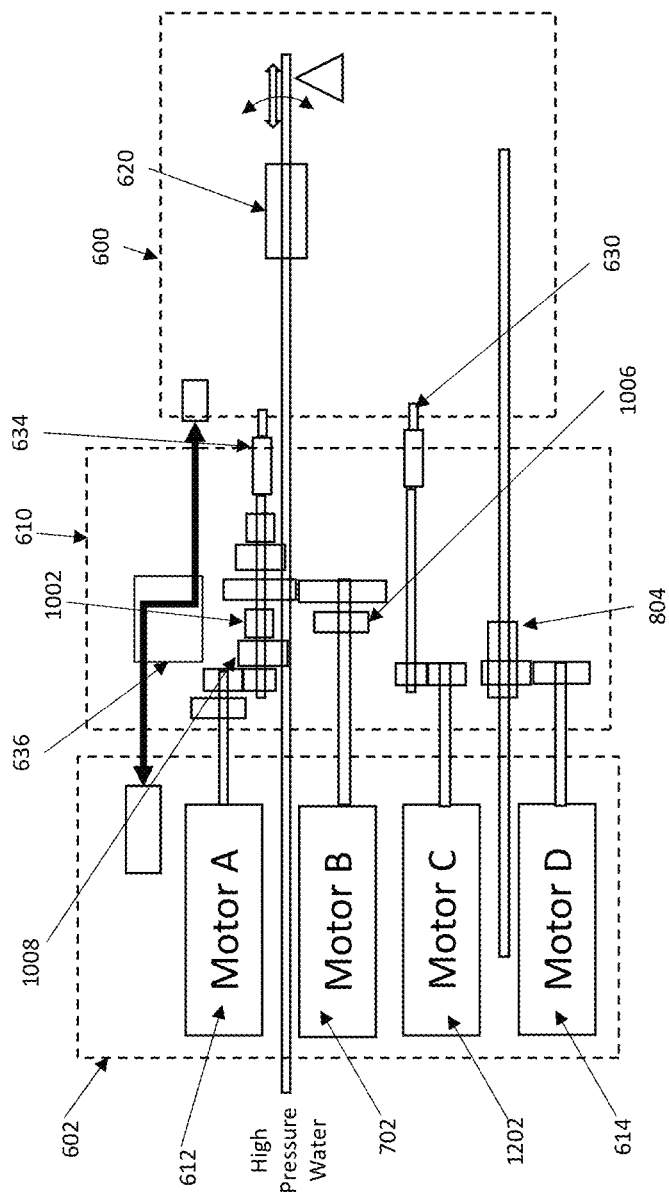
Figure 14:
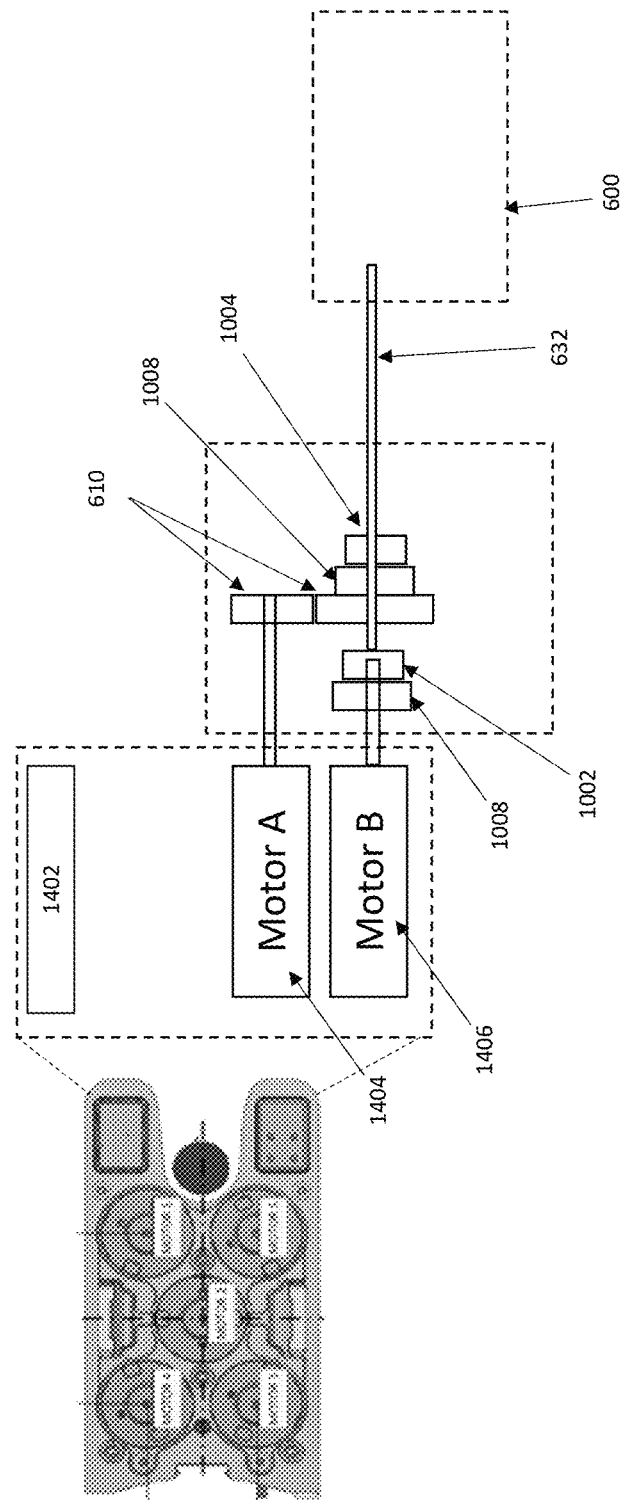
Figure 15:
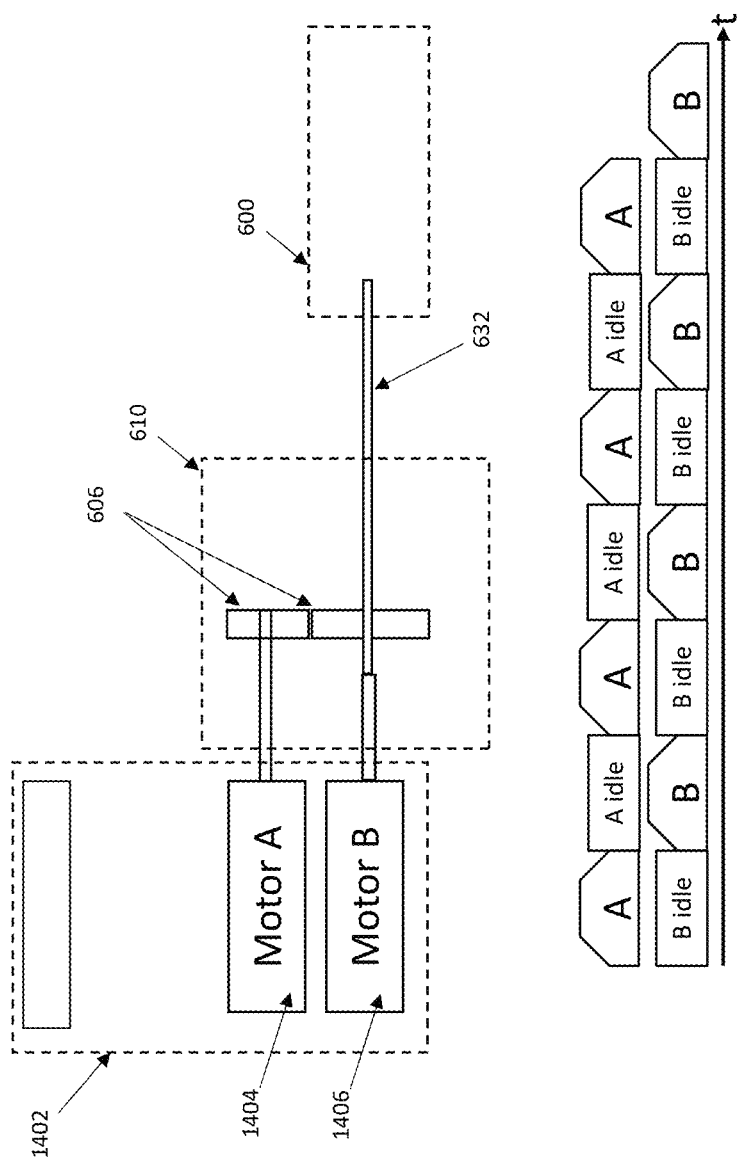
Figure 16:
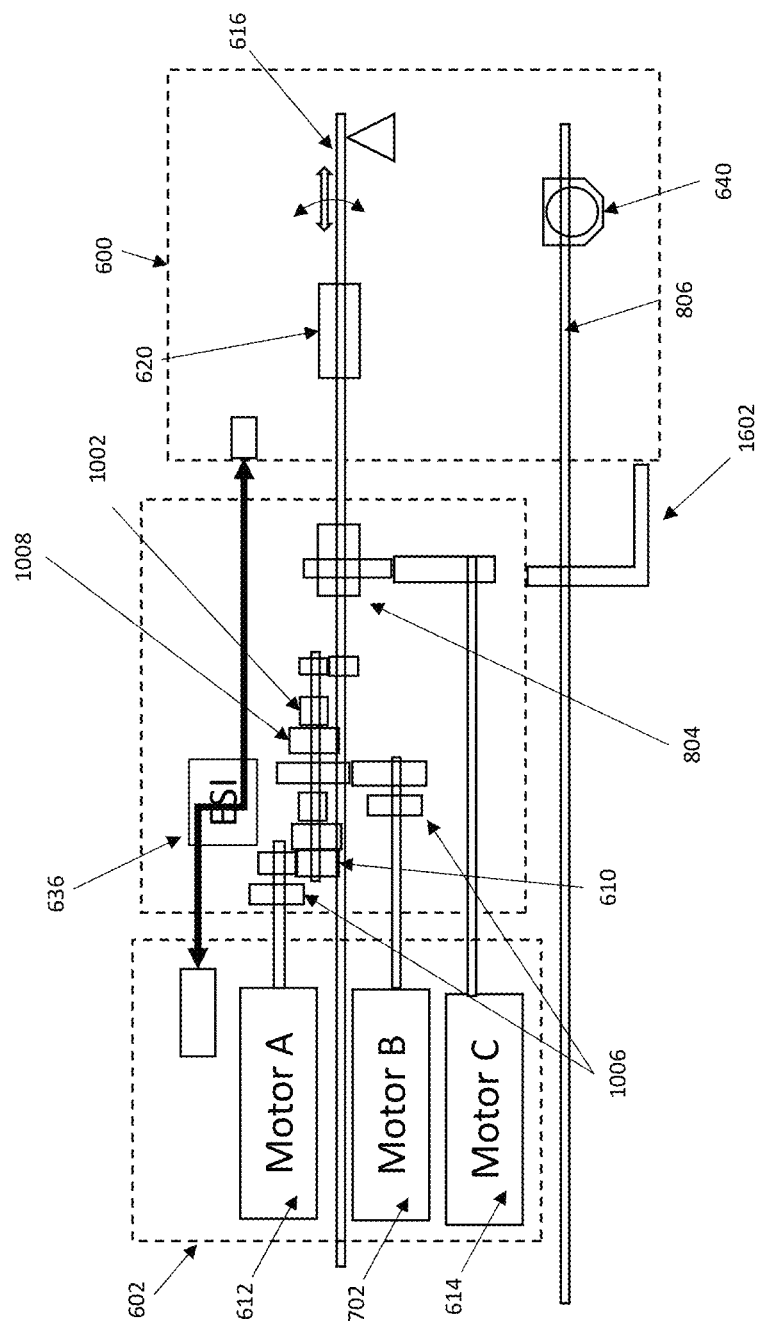
Figure 17:
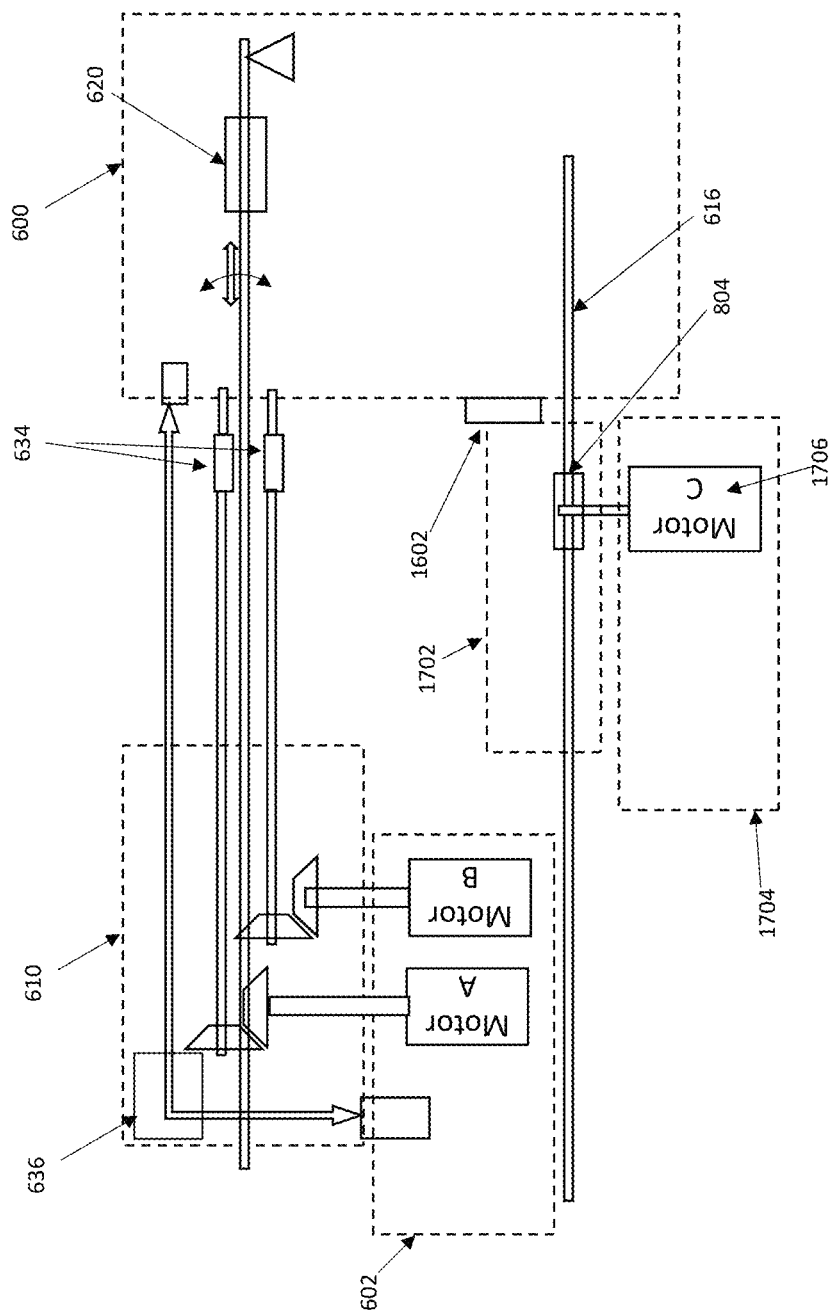
Figure 18:
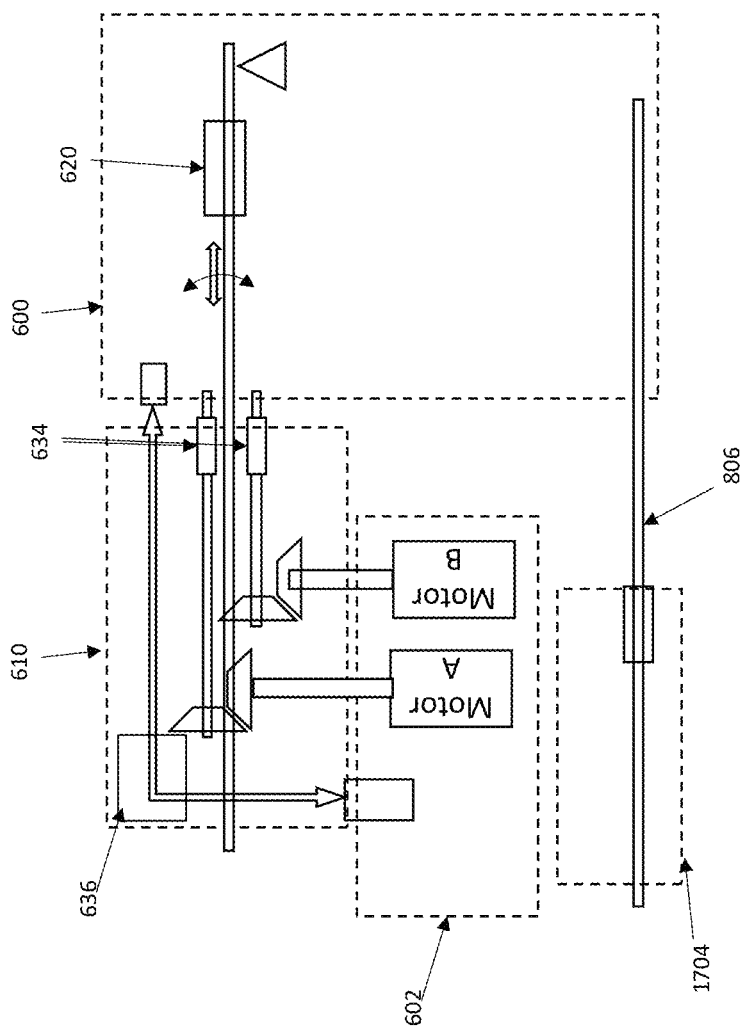
Figure 19:
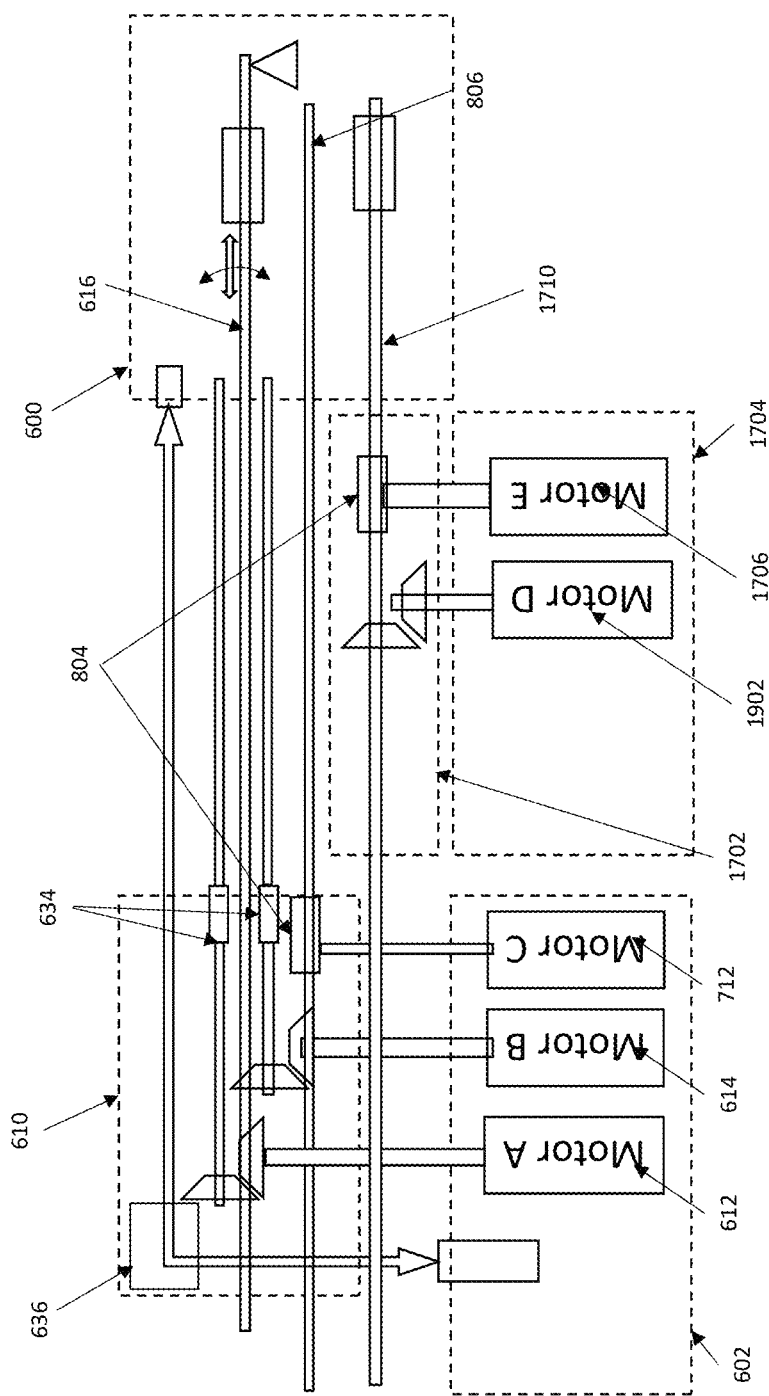
Figure 20:
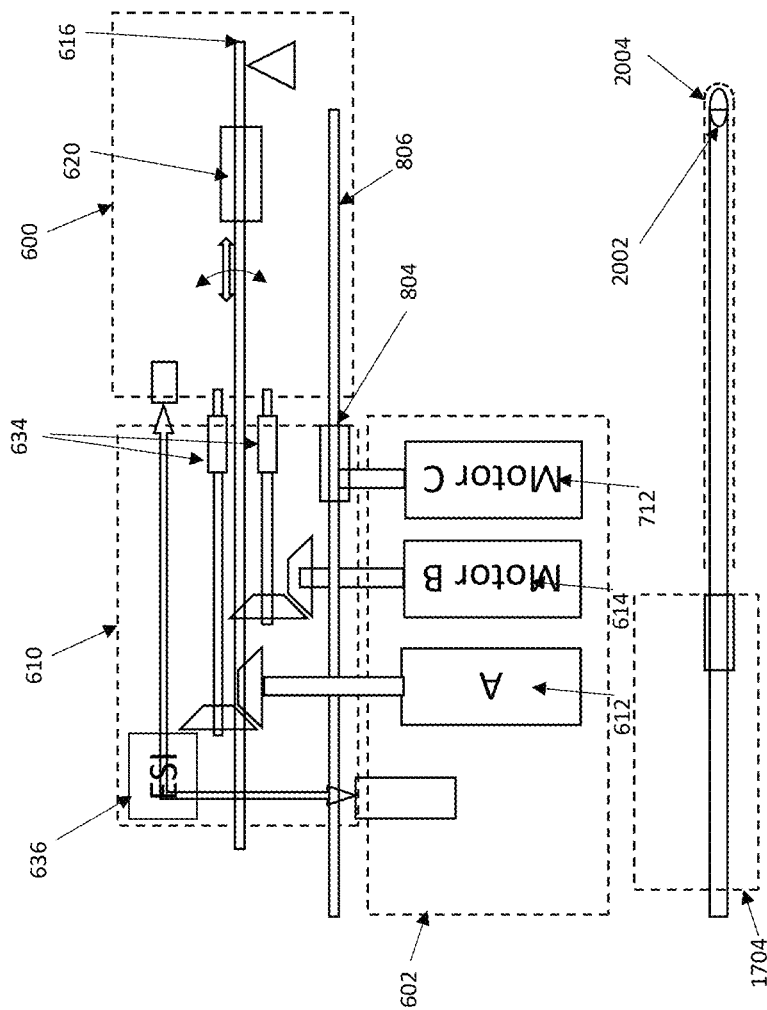
Figure 21:
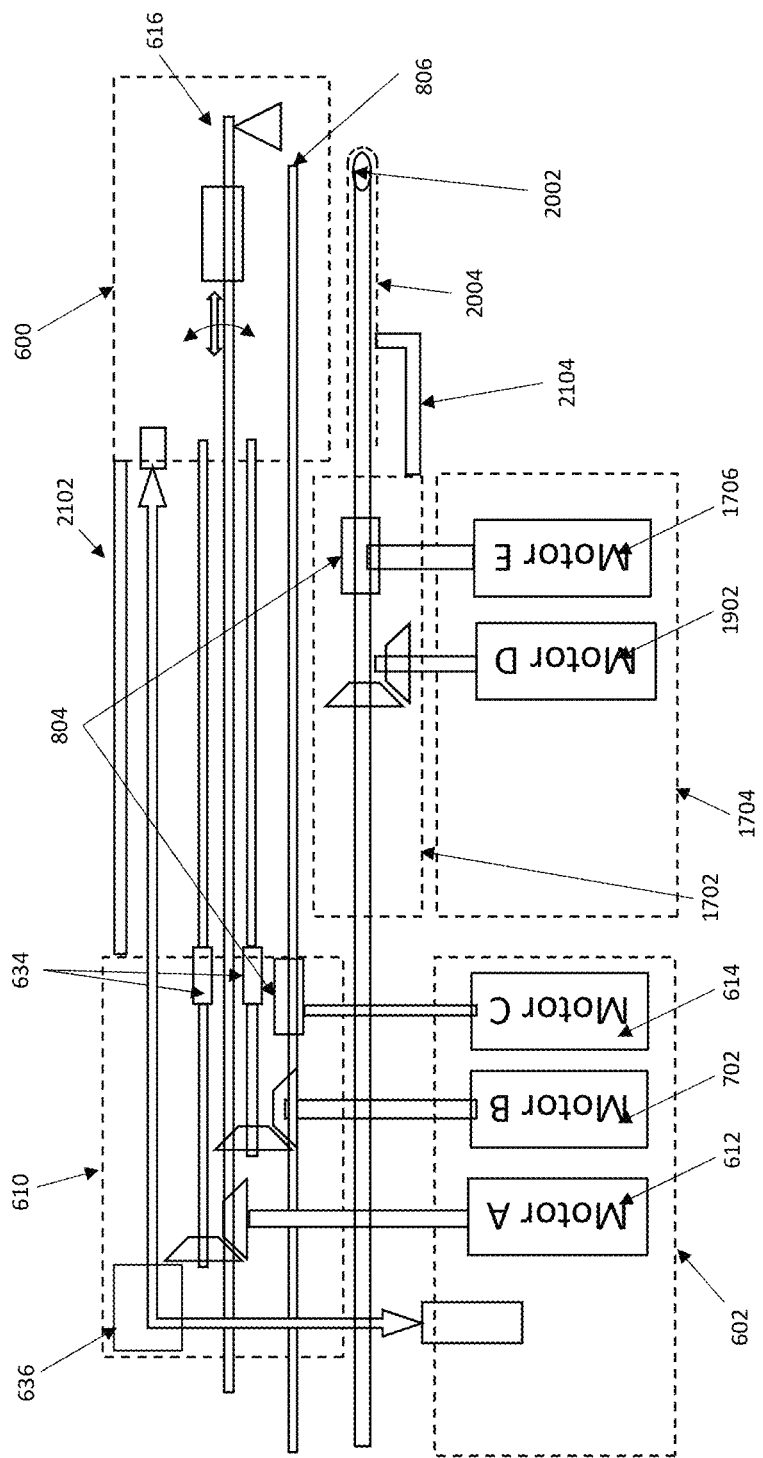
Figure 22:
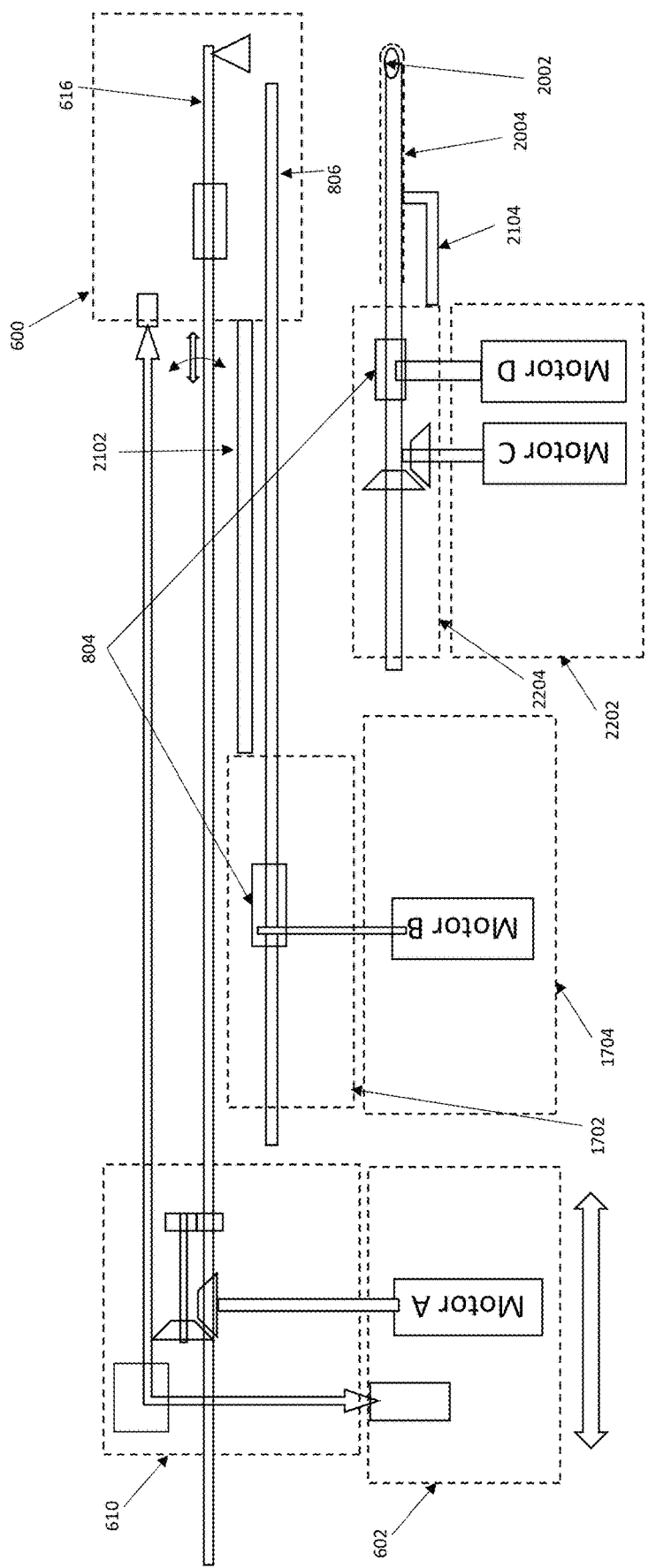

FIB. 7B schematically illustrates a system for coupling a handpiece to an instrument device manipulator by a parallel shaft transmission, in accordance with some embodiments;

FIG. 8 schematically illustrates a system for coupling a handpiece to an instrument device manipulator by a right-angled shaft transmission with a motorized scope, in accordance with some embodiments;

FIG. 9 schematically illustrates a system for coupling a handpiece to an instrument device manipulator by a parallel shaft transmission with a motorized scope, in accordance with some embodiments;

FIG. 10 schematically illustrates a system for coupling a handpiece to an instrument device manipulator by a right-angle shaft transmission providing for 2 rotational motors to be coupled to a surgical instrument, in accordance with some embodiments;

FIG. 11 schematically illustrates a system for coupling a handpiece to an instrument device manipulator by a parallel shaft transmission providing for 2 rotation motors coupled to a surgical instrument, in accordance with some embodiments;

FIG. 12 schematically illustrates a system for coupling a handpiece to an instrument device manipulator by a right-angle shaft transmission providing for 2 rotation motors coupled to a surgical instrument and a motorized scope, in accordance with some embodiments;

FIG. 13 schematically illustrates a system for coupling a handpiece to an instrument device manipulator by a parallel shaft transmission providing for 2 rotation motors coupled to a surgical instrument with a motorized scope, in accordance with some embodiments;

FIG. 14 schematically illustrates a system for coupling a handpiece to an instrument motor driver providing for 2 rotation motors, in accordance with some embodiments;

FIG. 15 schematically illustrates a system for coupling a handpiece to an instrument motor driver providing for 2 rotation motors that provide rapid motor direction switching, in accordance with some embodiments;

FIG. 16 schematically illustrates a system for coupling a handpiece to an instrument device manipulator by a parallel shaft transmission providing for 2 rotation motors, in accordance with some embodiments;

FIG. 17 schematically illustrates a system for coupling a handpiece with two instrument device manipulators and a driven scope, in accordance with some embodiments;

FIG. 18 schematically illustrates a system for coupling a handpiece with two instrument device manipulators with a right-angle shaft transmission and a scope actuated by one instrument device manipulator, in accordance with some embodiments;

FIG. 19 schematically illustrates a system for coupling a handpiece with two instrument device manipulators with a right-angle transmission coupled to one instrument device manipulator for controlling the handpiece, and a second instrument device manipulator for controlling a second treatment probe, in accordance with some embodiments, FIG. 20 schematically illustrates a system for coupling a handpiece with two instrument device manipulators, with one instrument device manipulator coupled to the handpiece with a right-angle transmission and another instrument device manipulator coupled to an imaging probe, in accordance with some embodiments;

FIG. 21 schematically illustrates a system for coupling a handpiece to an instrument device manipulator by a right-angle transmission and an imaging probe to another instrument device manipulator, in accordance with some embodiments; and FIG. 22 schematically illustrates coupling a handpiece and an imaging probe to three instrument device manipulators, in accordance with some embodiments.

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Embodiments of the present disclosure provide improved methods and apparatus for performing tissue diagnostic procedures or treatment such as tissue resection, for example prostate tissue resection. The methods and apparatus disclosed herein are well suited for many types of surgical procedures, and can be incorporated into many prior systems and methods. While some embodiments of the instruments of the present disclosure are directed to transurethral treatment of the prostate, some aspects of the present disclosure may also be used in conjunction with instruments used to treat and modify other tissues and associated organs such as, but not limited to, brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

The presently disclosed methods and apparatus are well suited for instruments used for treating many types of tissue with an energy source. The tissue may comprise soft tissue, such as glandular tissue or capsular tissue, or hard tissue such as bone or blockages, such as kidney stones, for example. The energy source may comprise one or more of a laser beam, a water jet, an electrode, ultrasound, high intensity focused ultrasound, mechanical vibrations, radiofrequency (RF) energy an ultrasound transducer, microwave energy, cavitating energy such as a cavitating water jet or ultrasonic cavitations, radiation such as ionizing radiation from a radioisotope, or ion energy from ionization electrodes or plasma energy from plasma electrodes. The presently disclosed methods and apparatus are well suited for performing lithotripsy to break up kidney stones, for example. The presently disclosed methods and apparatus are well suited for treatment with radiation, such as a radio isotope on the treatment probe. The radiation treatment can be provided on the probe and removed with the probe, or implanted from the treatment probe, for the treatment of cancer for example.

The presently disclosed methods and apparatus are well suited for attaching a treatment probe to a robotic arm for use in diagnostic or treatment procedures. For example, a robotic arm can be coupled to a suitable treatment probe to treat and/or remove kidney stones, such as by performing shock wave lithotripsy, cystoscopy and ureteroscopy, percutaneous nephrolithotomy or other treatment methodology for treating and/or removing kidney stones. Similarly, the disclosed methods and apparatus are well suited for attaching a treatment probe to a robotic arm for use in diagnosing, treating, and/or removing cancer. For example, the presently disclosed methods and apparatus are well suited to be used for hyperchemo targeted radiation, selective tissue removal, implantation of ablative materials, or other suitable technique for diagnosing, treating, or removing cancer. In some instances, the robotic arm can be used to perform cautery or coagulation with a suitable energy delivery probe, such as RF, laser, ultrasonic energy, waterjet, microwave energy, cavitating energy, or other forms of energy. These procedures may be performed with or without simultaneous image guidance. For example, a robotic arm can follow the same, or similar path, that a robotic arm used for resection. Because a location, orientation, and pathway of a robotic arm can be tracked, stored, and repeated, a subsequent procedure with a robotic arm without image guidance. For example, an energy source can provide tissue hemostasis treatment after, or during, a tissue resection procedure such as with a waterjet. The tissue hemostasis treatment may be performed without image guidance because the controller of the robotic arms has already determined the resected cavity and can apply the hemostatic treatment by following the contours of the resected cavity. The hemostatic treatment may be performed while a waterjet resection is occurring, such as by a linked probe that follows behind the waterjet probe, or may be performed after a tissue resection procedure is complete.

In some embodiments, an image-guided treatment system comprises a treatment probe and an imaging probe. The imaging probe may be configured to provide an image of the target site before, during, and/or after the treatment probe performs any of a number of suitable treatments, such as tissue collection, ablation, cauterization, hemostasis, or resection of the target tissue. The treatment probe and the imaging probe may each be coupled to robotic arms, also referred to herein as instrument device manipulators, under control of one or more computing devices, in order to enable more precisely controlled movement of one or both of the arms and to improve the safety and efficiency of treatment using the treatment system. The treatment probe and the imaging probe may instead or also be under the control of signals received from a joystick, GUI, or other form of manual controller. The treatment probe and the imaging probe may be coupled to a single instrument device manipulator or each may be coupled to an individual instrument device manipulator.

The robotic arms can be configured in many ways. Work in relation to the present disclosure suggests that a transrectal ultrasonic (TRUS) probe can exert force on a robotic arm. In some embodiments this force is related to force from the patient against the probe. In some embodiments this force is related to force caused by the practitioner surgeon moving the probe against and moving the tissue for the purpose of improving imaging or tissue position relative to the intended treatment. The length of the probe can result in a corresponding torque on the robotic arm.

The present inventors have conducted experiments to determine the amount of force from the TRUS probe that can be applied to the robotic arm. This force can be measured at a motor mount exterior to the patient, for example. The force can range from 0 to about 5 kilograms (0-49 Newtons), depending on the surgical placement of the probe and patient. In some embodiments, the distance from the arm to the point of contact with prostate corresponds to an amount of torque on the arm.

Instrument positioning can have three categories of motion control and capability in accordance with some embodiments disclosed herein. The three categories of motion generally comprise a 1) coarse motion capability for movement, storage and preparation for surgery, 2) an intermediate movement capability for aligning the probe with the patient and inserting the probe into the patient, and 3) a fine movement capability corresponding to positional tolerances for accurate surgery.

Coarse motion capability allows for storage below and adjacent to the table and during patient positioning, for example.

Intermediate motion allows for instrument positioning with respect to the patient on the surgical support structure, e.g. an operating room ("OR") table, for example when the system is being prepared and positioned for patient entry. A typical range of position for the TRUS probe or any suitable surgically invasive probe is to have free motion for insertion into the patient, which can be describe with a X,Y,Z coordinate system. With an appropriate coordinate reference system, the entry to a lumen of the patient may correspond to values of 0, 0, 0 in an X,Y,Z coordinate system. The coordinate reference may also comprise angular coordinate references of X',Y',Z'. The entry to the lumen may comprise an anus of the patient. With an anal entrance at 0,0,0 and the probe colinear with the patient axis, the intermedia motion may comprise an X motion tolerance of +/−2 to 15 cm, Y motion tolerance of +/−2 to 15 cm, and Z motion tolerance of +/−2 to 30 cm. In some embodiments, the X and Y motion corresponds to translation of the probe along the X and Y coordinate references. The Z axis position corresponds to movement along an axis of the lumen, and may correspond to advancement and retraction of the probe along the body lumen, e.g. translational movement into and out of the patient. With an angular adjustment of X',Y', Z', the angular position capability may comprise X'+/−zero to 30 degrees, Y'+/−zero to 30 degrees, Z'+/−zero to 30 degrees, with respect to the natural axis of the patient. Work in relation to the present disclosure suggests that a probe with these angular capabilities can be manipulated by a user for insertion into the patient.

In some embodiments, the fine movement capability and tolerances correspond to a configuration of the robotic probe and arms with the probe positioned in the patient, for example during tissue resection and imaging. When the system is in use with instruments positioned for diagnosis and treatment, the sensors and controls and described herein can be configured to prevent tissue damage, and also to position treatment probe and imaging probe to obtain reliable images, e.g. optimal images, and the treatment and imaging probes can be precisely positioned and firmly held in position against tissue pressures. The X,Y,Z reference frame can be centered on the lumen entrance at 0,0,0 (and the probe colinear with the patient axis). In some embodiments, X motion tolerance is +/−0 to 5 cm; the Y motion tolerance is +/−0 to 5 cm; and Z motion tolerance is +/−0 to 15 cm. The X and Y motion generally corresponds to translation of the probe, and the Z axis corresponds to advancement and retraction of the probe in and out of the patient. The corresponding angular adjustment ranges for X',Y',Z' are X'+/−zero to 10 degrees, Y'+/−zero to 10 degrees, and Z'+/−zero to 15 degrees, with respect to a natural axis of the patient, for example with reference to a midline of the patient with the Z axis extending along the midline of the patient. While the above values represent ranges of motion, the robotics arms and surgical probes may provide tighter tolerances for fixed position configurations of the probe. For example, when the probe is intended to be held in a fixed position, the rotational tolerances can maintain one or more of X',Y',Z' within a within +/−5° tolerance or less, e.g. +/−3°. With respect to translational movement, the manually set position can be maintained to a positional tolerance of 5 mm or less, 3 mm or less, or 2 mm or less for one or more of the X, Y, Z axes, for example. In some embodiments, these tolerances are maintained for each of X, Y, Z and X', Y', Z'. In some embodiments, the probe is manually set, and the translational and rotational tolerances are maintained to within the above values, which can improve the accuracy of the tissue treatment and associated imaging. These tolerance may correspond a maximal structural relaxing or loading of the arm with the probe mounted thereon, for example.

The probe can be manipulated and inserted into the patient in many ways. For example the probe can be manipulated manually, and the robotic arm moved into alignment with the probe and coupled to the probe, with the probe maintaining the above tolerances when released by the user and the arm subsequently supporting the full load of the patient and probes. The arm can be brought into alignment with the probe manually, or with at least some automation in which sensors and guidance circuitry are used to bring the arm into alignment with the probe held by the user. The arm may comprise a coupling structure to engage the probe with 6 degrees of freedom, such that a coupling structure on the arm can be brought into precise alignment with the coupling structure on the probe. The coupling structures can be subsequently engaged and coupled to each other in response to detection of the alignment. In some embodiments, sensors are provided on one or more of the arm or the probe to detect alignment between the arm and probe, and the coupling structures engaged in response to the detected alignment. The robotic arm may comprise a linkage coupled to a processor, in which the processor controls movement of the arm and brings the arm into alignment with the probe held by the user.

In some embodiments, the urethral probe has similar dimensional, motion and tolerance capabilities to the TRUS probe.

In some embodiments, the probe comprises a mass within a range from about 250 grams to 1500 grams, and the arm maintains the tolerances described herein with the probe comprising the mass within this range.

The robotics arms as described herein can improve alignment between the treatment probe and the imaging probe, which may comprise sagittal plane of an imaging TRUS probe. For example, the treatment probe be aligned substantially coplanar along the sagittal plane of the imaging probe. This coplanarity can provide clear imaging and alignment of coordinates of the treatment probe and imaging probe. In some embodiments, the tolerance of this coplanarity is related to the combination of the width of the treatment probe and the width of the imaging plane capability, e.g. width of the image captured with ultrasound beam forming. The relative position of the TRUS to the treatment probe can be substantially parallel and aligned within an angular tolerance. The alignment can be within a range from +/−zero (parallel) to about 30 degrees. In some embodiments, the elongate axis of the treatment probe and TRUS probe are aligned in a substantially co-planar configuration, with the separation distance between the probes varying along the length of the imaging and treatment probes. For example, the distal tip of the treatment probe can be farther away from the TRUS probe and the proximal end closer to the TRUS probe, in which the two probes are inclined relative to each other, although substantially coplanar. The inclination between the two probes can be related to the tissue constraints of natural orifices of each unique human. The distances between the entrances to the naturally available orifices can vary, for example within a range from about 5 cm to about 25 cm separation.

In some embodiments, the imaging probe and the treatment probe are aligned so that the treatment probe is within the field of view of the imaging probe. In some embodiments, the alignment is configured to maintain the treatment probe within a field of view of the imaging probe. In some embodiments, the treatment probe is configured to move to a position and the imaging probe is configured to maintain the treatment probe within the field of view.

Figure 1:
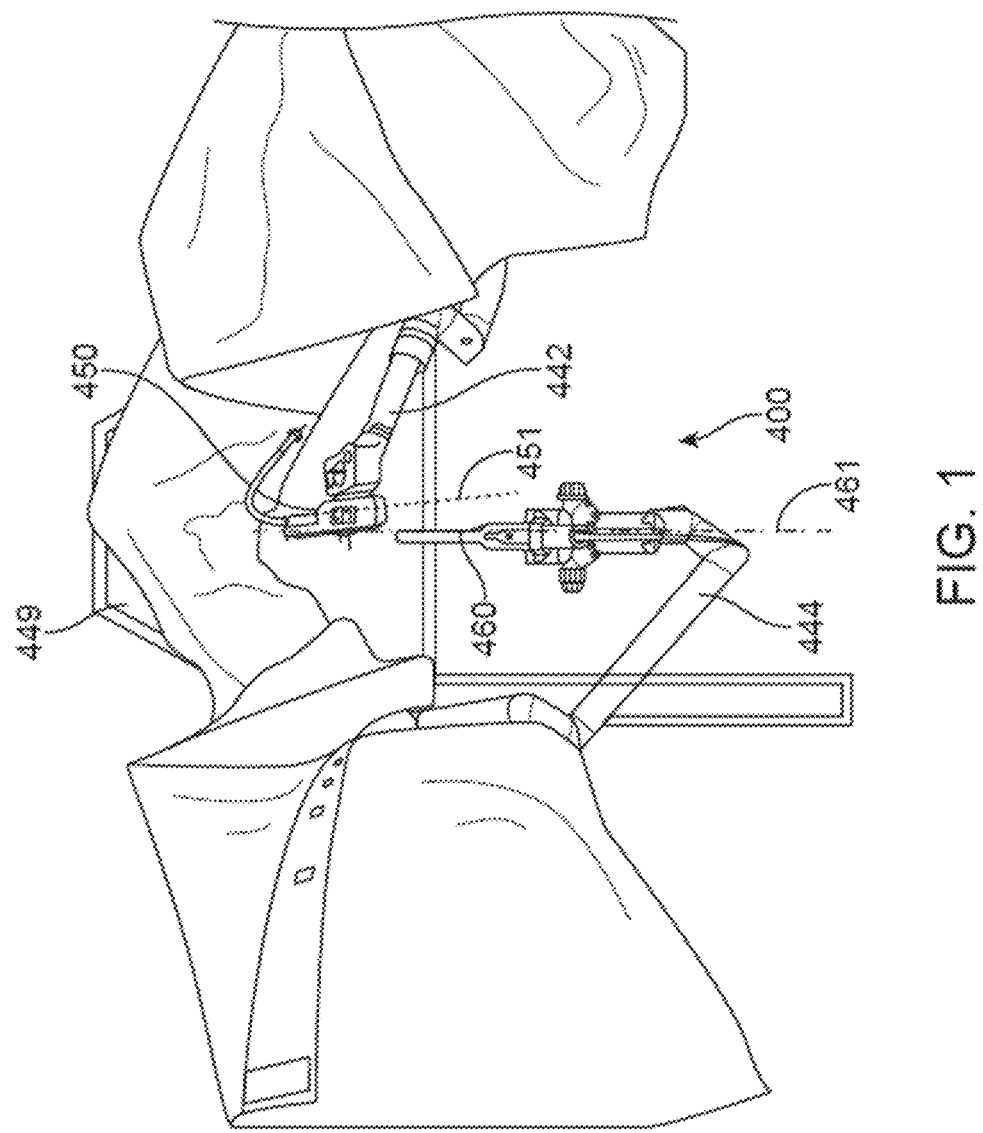
FIG. 1 shows a front view of a system for performing tissue resection in a patient, in accordance with some embodiments.

FIG. 1 shows an exemplary embodiment of a system 400 for performing tissue resection in a patient. The system 400 may comprise a treatment probe 450 and an imaging probe 460. The treatment probe 450 may be coupled to a first arm 442, and the imaging probe 460 coupled to a second arm 444. One or both of the first arm 442 and the second arm 444 may comprise robotic arms, also referred to herein as instrument device manipulators, whose movements may be controlled by one or more computing devices operably coupled with the arms. The treatment probe 450 may comprise a device for performing any suitable diagnostic or treatment procedure, and may include resecting, collecting, ablating, cauterizing, or a combination of these or other treatments to tissue from a target site within a patient. The treatment probe 450 may be configured to deliver energy from the treatment probe 450 to the target tissue sufficient for removing the target tissue. For example, the treatment probe 450 may comprise an electrosurgical ablation device, a laser ablation device, a transurethral needle ablation device, a water jet ablation device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
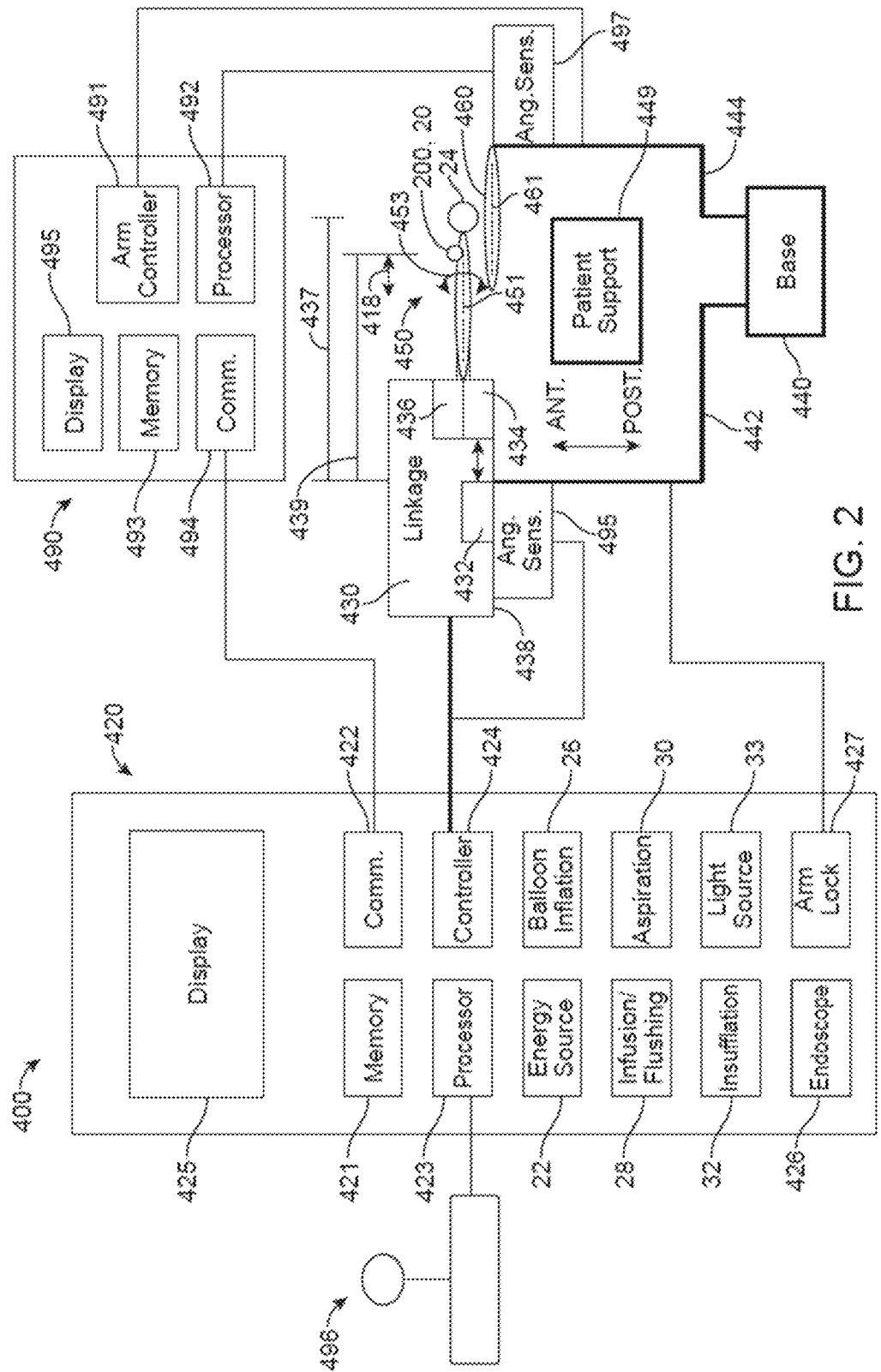
FIG. 2 schematically illustrates a system for performing tissue resection in a patient, in accordance with some embodiments.

FIG. 2 schematically illustrates an exemplary embodiment of the system 400 for performing tissue resection in a patient. The system 400 comprises a treatment probe 450 and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such the treatment or imaging probe can be desirably rotated and translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 424. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 32 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. The probe 450 may comprise a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed to the substantially constant distance 437 to the anchor 24. The substantially fixed distance 437 between the anchor 24 and the fixed first portion 432 of the linkage allows the treatment to be accurately placed. The first portion 432 may comprise a linear actuator to accurately position the high-pressure nozzle 200 in the energy delivery region 20 at a desired axial position along an elongate axis 451 of treatment probe 450.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust in manner 418 in response to computer control to set a target location along the elongate axis 451 of the treatment probe referenced to anchor 24. The first portion of the linkage remains fixed, while the second portion 434 adjusts the position of the energy delivery region 20 along the axis 451. The third portion of the linkage 436 adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 495.

In order to facilitate precise control of the treatment probe and/or the imaging probe during treatment of the patient, each of the treatment probe and the imaging probe may be coupled to a robotic, computer-controllable arm. For example, referring to system 400 shown in FIG. 2, one or both of the first arm 442 coupled to the treatment probe 450 and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

Either or both robotic arms may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic arms, the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

Figure 3B:
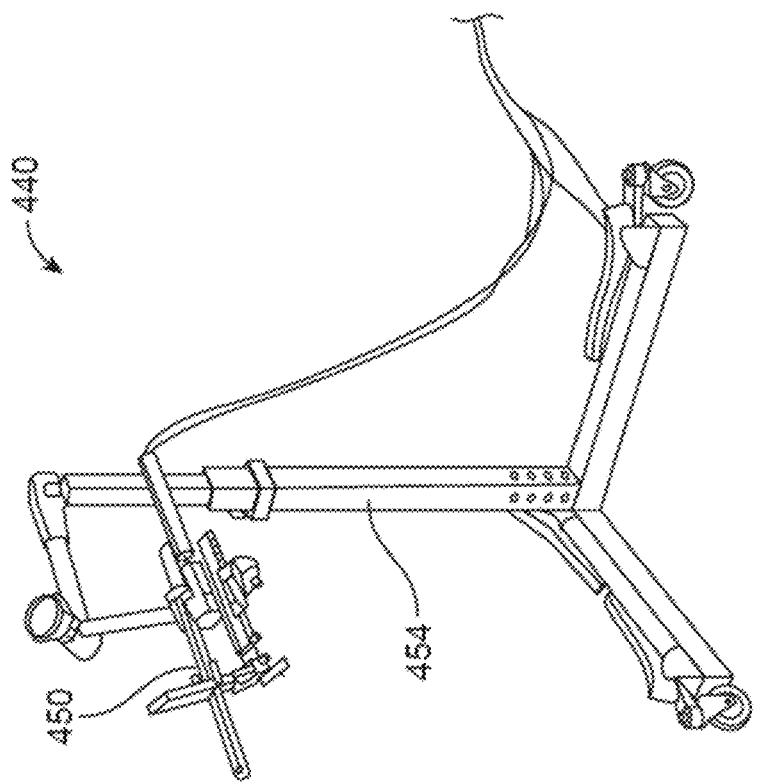
FIGS. 3A and 3B show perspective views of a common base or mount for supporting one or more robotic arms, in accordance with some embodiments.
Figure 3A:
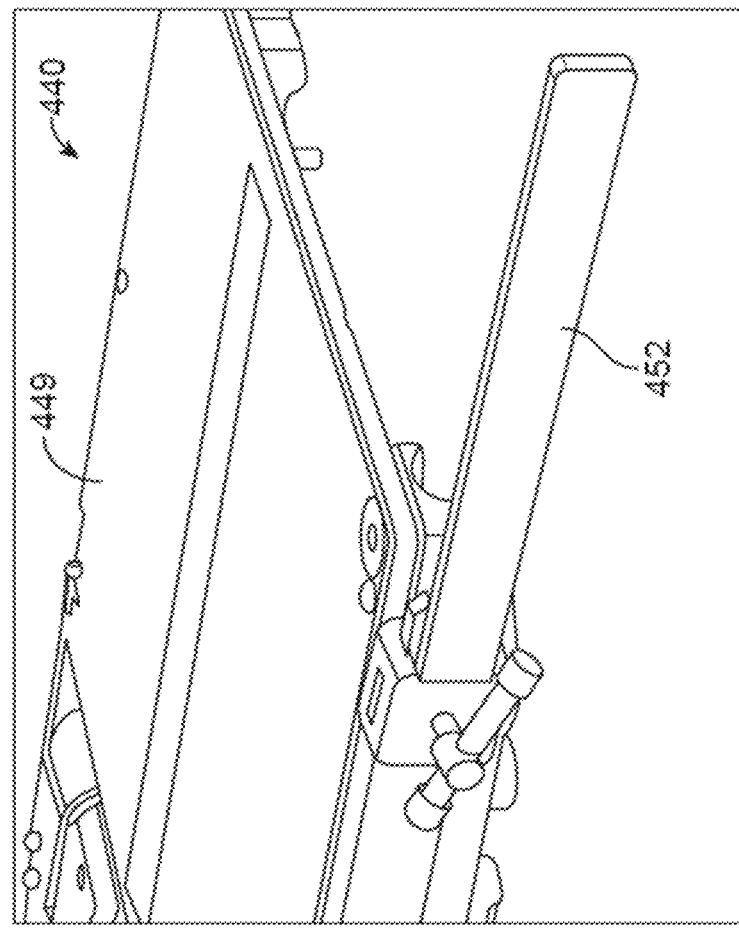

FIGS. 3A and 3B show exemplary embodiments of a common base or mount 440 for supporting one or more robotic arms of an image-guided treatment system as disclosed herein. FIG. 3A shows a patient support 449 comprising one or more rails 452. The patient support 449 may comprise a surgical table or a platform. One or more robotic arms associated with one or more of the treatment probe or the imaging probe may be mounted to the rails 452, such that the rails function as the common base 440. FIG. 3B shows a common base 440 comprising a floor stand 454 configured to couple to the first robotic arm connected to the treatment probe and/or the second robotic arm connected to the imaging probe. The floor-stand 454 may be positioned between the patient's legs during the treatment procedure.

Figure 4A:
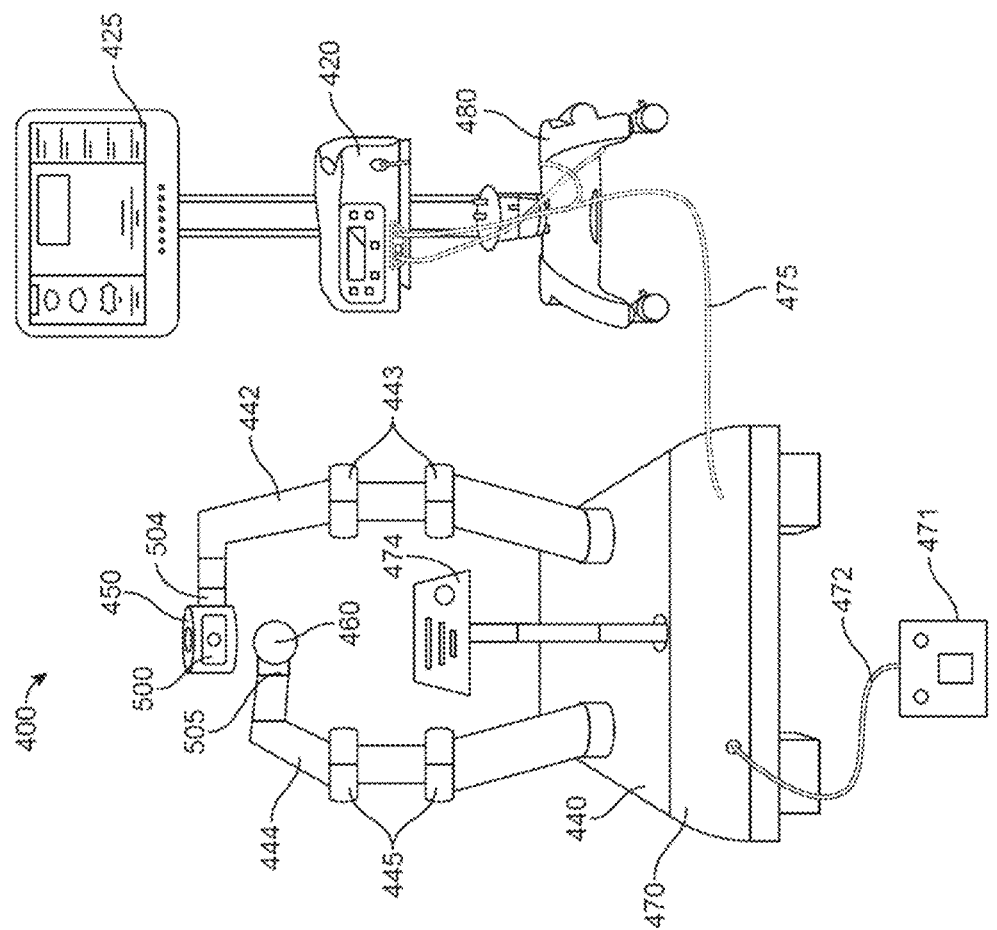
FIGS. 4A and 4B illustrate a perspective and side view, respectively, of a system for performing tissue resection in a patient that comprises a mobile base, in accordance with some embodiments.
Figure 4B:
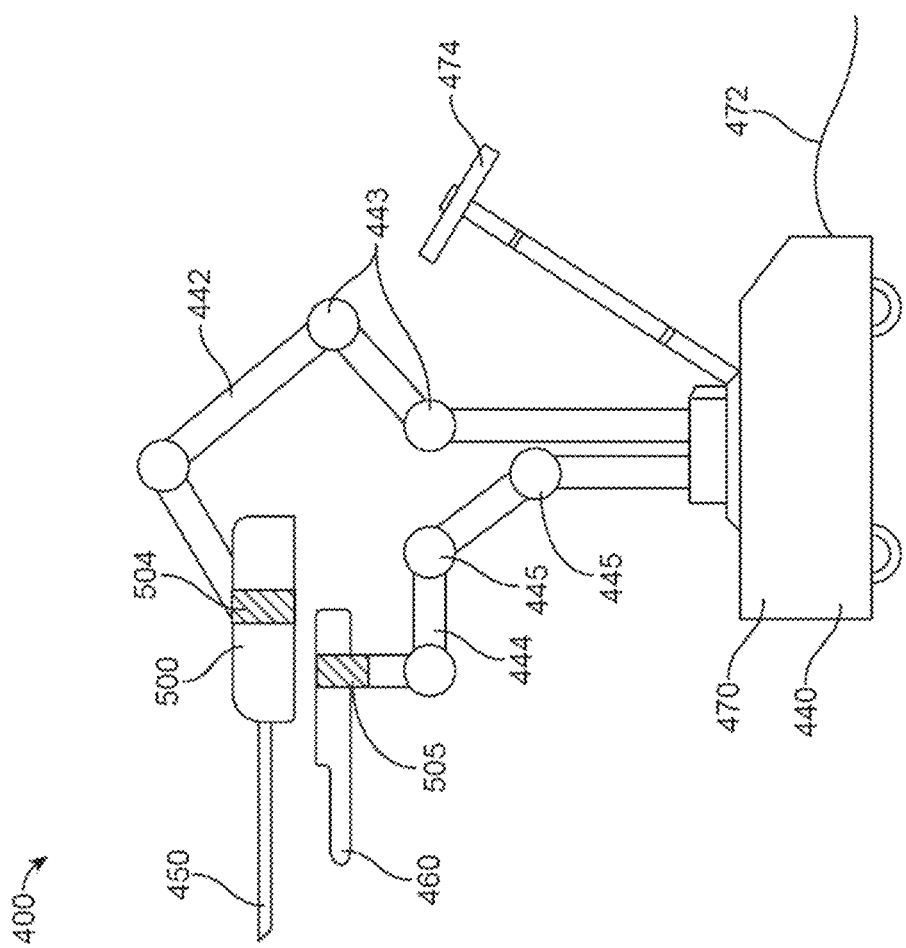

FIGS. 4A and 4B illustrate an exemplary embodiment of a treatment system 400 as described herein comprising a mobile base 470. FIG. 4A is a front view and FIG. 4B is a side view of the treatment system 400. The treatment system 400 comprises a treatment probe 450 coupled to a first robotic arm 442, and an imaging probe 460 coupled to a second robotic arm 444. The first robotic arm 442 and the second robotic arm 444 each comprises a proximal end and a distal end, the distal end coupled to the treatment probe 450 and the imaging probe 460, respectively, and the proximal end coupled to a common base 440 comprising a mobile base 470. The first robotic arm 442 may comprise a first arm coupling structure 504 to couple to the treatment probe 450, and the second robotic arm 444 may comprise a second arm coupling structure 505 to couple to the imaging probe 460. The treatment probe 450 may be coupled to the distal end of the first robotic arm 442 via an attachment device 500, which may comprise a linkage configured to affect movement of the treatment probe as described herein (e.g., rotation, translation, pitch, etc.). Coupling of the treatment probe 450 to the first robotic arm 442 may be fixed, releasable, or user adjustable. Similarly, coupling of the imaging probe 460 to the second robotic arm 444 may be fixed, releasable, or user adjustable.

The first robotic arm 442 may articulate at one or more first arm joints 443. The imaging arm 444 may articulate at one or more second arm joints 445. Each arm joint 443 or 445 may be operably coupled with a computer-controllable actuator, such as a stepper motor, to affect movement at the joint. Each arm joint 443 or 445 may comprise one of a variety of kinematic joints including but not limited to a prismatic, revolute, parallel cylindrical, cylindrical, spherical, planar, edge slider, cylindrical slider, point slider, spherical slider, or crossed cylindrical joint, or any combination thereof. Moreover, each arm joint 443 or 445 may comprise a linear, orthogonal, rotational, twisting, or revolving joint, or any combination thereof.

The system 400 may further comprise a console 420 as described herein, which may be supported by a mobile support 480 separate from the mobile base 470. The console 420 may be operably coupled with the mobile base 470 via a power and communication cable 475, to allow control of the treatment probe 450 coupled to the mobile base via the first robotic arm. The treatment console 420 comprises a processor and a memory having stored thereon computer-executable instructions for execution by the processor, to control various modules or functionalities of the treatment console, such as an energy source, infusion/flushing control, aspiration control, and other components as described herein with reference to FIG. 2. The treatment console 420 may further comprise a display 425 in communication with the processor. The display 425 may be configured to display, for example, one or more of: subject vital signs such as heart rate, respiratory rate, temperature, blood pressure, oxygen saturation, or any physiological parameter or any combination thereof; status of a procedure; one or more previously taken images or sequence of images of a treatment site from one or more views; one or more real-time images or sequence of images of the treatment site from one or more views acquired by the imaging probe 460; a set of treatment parameters including but not limited to a treatment mode such as cutting or coagulating, an intensity of treatment, time elapsed during treatment, time remaining during treatment, a depth of treatment, an area or volume of the treatment site that has been treated, an area of the treatment site that will be treated, an area or volume of the treatment site that will not be treated, location information of the treatment probe 450 or the imaging probe 460 or both; treatment adjustment controls such as means to adjust the depth of treatment, the intensity of treatment, the location and/or orientation of the treatment probe 450, the depth of imaging, or the location and/or orientation of the imaging probe 460, or any combination thereof; or system configuration parameters.

The mobile base 470 may further comprise one or more computing devices to control operation of the one or more robotic arms. For example, the mobile base may comprise processors and a memory having stored thereon computer executable instructions for execution by the one or more processors. The memory may have stored thereon instructions for operating the one or more robotic arms coupled to the mobile base. The processor may be operably coupled with the robotic arms via suitable electromechanical components to affect movement of the robotic arms. For example, each of the one or more joints of a robotic arm may comprise a step motor, and the processor may be operably coupled with the step motor at each joint to actuate the motor by a specified increment in a specified direction. Alternatively, the one or more robotic arms may be operably coupled with one or more processors of the console 420 or a separate imaging console (such as imaging console 490 shown in FIG. 2), wherein the one or more console processors may be configured to execute instructions for controlling movement of the one or more robotic arms, and may communicate the instructions to the robotic arms via communication circuitry (such as communication circuitry 422 of console 420 or communication circuitry 494 of console 490 shown in FIG. 2). The computer executable instructions for controlling movement of the robotic arms may be pre-programmed and stored on a memory, or may be provided by a user via one or more user inputs before or during treatment of the patient using the treatment system.

The one or more computing devices operably coupled with the first and/or second robotic arms may be configured to control movement of the arms so as to adjust the pitch, yaw, roll, and/or linear position of the treatment probe and/or imaging probe along the target site.

The mobile base 470 may comprise one or more user input devices to enable a user to control movement of the robotic arms under computer instructions. For example, as shown in FIGS. 4A and 4B, the mobile base may comprise a keyboard 474 and/or a footswitch 471, the footswitch operably coupled with the mobile base via a footswitch cable 472. The keyboard 474 and the footswitch 471, independently or in combination, may be configured to control operation of the first robotic arm 442 and/or the second robotic arm 444, for example via articulation of one or both robotic arms at one or more joints. The keyboard and the footswitch may be in communication with the one or more processors configured to control movement of the robotic arms. When a user inputs instructions into the keyboard and/or the footswitch, the user instructions can be received by the one or more processors, converted into electrical signals, and the electrical signals may be transmitted to the one or more computer-controllable actuators operably coupled with the one or more robotic arms. The keyboard and/or the footswitch may control movement of one or both arms towards or away from a treatment position, a position of interest, a predetermined location, or a user-specified location, or any combination thereof.

Optionally, the keyboard 474 and the footswitch 471, independently or in combination, may be configured to control operation of the treatment probe 450 and/or imaging probe 460. For example, the keyboard 474 and/or footswitch 471 may be configured to start, stop, pause, or resume treatment with the treatment probe. The keyboard 474 and/or footswitch 471 may be configured to begin imaging or freeze, save, or display on the display 425 an image or sequence of images previously or currently acquired by the imaging probe.

The mobile base 470 and the mobile support 480 of the console 420 may be independently positionable around a patient, supported by a patient support 449 such as a platform. For example, the mobile base 470, supporting the first and second robotic arms and the treatment and imaging probes, may be positioned between the patient's legs, while the mobile support 480 carrying the console 420 and the display 425 may be positioned to the side of the patient, such as near the torso of the patient. The mobile base 470 or the mobile support 480 may comprise one or more movable elements that enable the base or the support to move, such as a plurality of wheels. The mobile base 470 may be covered with sterile draping throughout the treatment procedure, in order to prevent contamination and fluid ingress.

FIGS. 5A-5B show an exemplary coupling between a treatment probe 450 and a first robotic arm 442. FIG. 5A shows the treatment probe uncoupled from the robotic arm. FIG. 5B shows the treatment probe coupled to the robotic arm. As shown, the treatment probe 450 may be coupled to the robotic arm 442 with an attachment device 500 which may comprise a reusable motor pack. The treatment probe 450 may be removably coupled to the attachment device 500. The attachment device may further comprise a connector 502 configured to couple to the robotic arm and lock the attachment device in place. The robotic arm 442 may comprise a coupling structure 504 disposed at the distal end of the arm, configured to lockingly receive the connector 502 of the attachment device 500. Once the treatment probe and the robotic arm are coupled together, movement of the treatment probe may be controlled by moving the robotic arm (e.g., by articulating one or more joints of the robotic arm under computer control).

In some embodiments, the treatment probe is coupled to the robotic arm via a quick release mechanism, such that the coupling between the probe and the robotic arm is capable of a quick disconnect in order to prevent injury to the patient in case the robotic arm loses position or otherwise fails to operate correctly. The treatment probe and the robotic arm may be coupled to one another in many ways such as mechanically (e.g., a broom clip) and/or magnetically. For example, in the embodiment shown in FIGS. 5A and 5B, the coupling structure 504 may comprise a slot 506 having a magnet 508 disposed therein, and the connector 502 may comprise a ferromagnetic fixture configured to fit within the slot 506 to engage the magnet 508. The coupling structure 504 may further comprise a latching mechanism 510 to selectively engage or disengage the connector 502 with the magnet 508. For example, as shown in FIGS. 5A and 5B, the latching mechanism 510 may comprise a rotatable knob that can be rotated to affect engagement of the magnet 508 of the coupling structure 504 with the connector 502 of the attachment device 500. The latching mechanism may be automatically or manually engaged or disengaged by a user to couple or de-couple, respectively, the attachment device 500, and hence the treatment probe 450 coupled thereto, to the robotic arm 442. In some embodiments, the coupling structure 504 may be operably coupled with the one or more computing devices configured to control the robotic arm, and the one or more computing devices may comprise instructions to release the coupling of the coupling structure to the probe when an error is detected in the operation of the robotic arm.

In some embodiments, the first robotic arm 442 may be configured to automatically locate the treatment probe 450 in response to sensor location data from one or more of the attachment device 500 or coupling structure 504. The first robotic arm 442 may be operated in a "seek" mode, for example, to locate the attachment device 500. In some embodiments, the probe comprises one or more fiducial targets and the robotic arm comprises corresponding sensors of sufficient resolution and positioning to identify the relative position of the probe in 3D space. In some embodiments, the processor is configured with instructions to seek the treatment probe or imaging probe with the mounting structures on the robotic arm while the user holds the probe steady, for example when the probe has been positioned in the patient.

The sensors on the robotic arm such as the first robotic arm 442 and sensors on the probe such as the treatment probe can be arranged in many ways.

The processor can be coupled to the sensors near the end of the robotic arm or on the probe to dynamically update the relative location during the movement of the robot arm while seeking to engage the probe on the arm. The sensors on the robotic arm may comprise a plurality of sensors comprising one or more of capacitive, capacitive displacement, doppler, inductive, magnetic, optical, radar, sonar, ultrasonic or Hall effect sensors, in order to determine relative distances between the robotic arm and the probe. In some embodiments the probe comprises a plurality of targets and the sensors are configured to generate signals in response to distances from the plurality of targets. Alternatively, or in combination, the sensors can be located on the probe and the targets on the robotic arm. In some embodiments, the sensors comprise close contact mechanical sensors to confirm docking of the probe on the robotic arm or in proximity to the arm, for example to sense the position of the probe in relation to the robotic arm when the probe and arm are within a few millimeters of docking with each other. The close contact mechanical sensors may comprise one or more of micro-motion switches, whisker touch sensors, or a pin-in-hole contact switch. In some embodiments, the probe and robotic arm comprise an integrated locking mechanism to provide a non-movement locking engagement at the final position of contact. The integrated locking mechanism may comprise one or more of magnetics, electromagnetics, a latching, screw such as a multi turn latching screw or quarter turn locking screw, a vacuum, or other mechanical means of reversible attachment as will be understood by one of ordinary skill in the art.

In some embodiments, a plurality of sensors is used, such as one or more sensors for near, one or more sensors for intermediate and one or more sensors for far separation distances between the probe and the robotic arm. A coarse location sensor can be used to determine the approximate location of the probe, e.g. a beacon. One or more sensors can be used for fine location positioning of the probe in relation to the robotic arm, e.g. proximity sensors. In some embodiments, one or more markers on the probe are used with a camera and machine vision detection of the one or more markers.

In some embodiments, coarse location sensors may be provided which may be an infrared (IR) beacon which enables the coarse positional spatial location for homing detection of the robotic arm to the probe. In some cases, a homing beacon, such as an IR beacon, allows for homing across larger distances as compared to a sensor that may rely on visual recognition of fiducials.

In some embodiments, a docking detection sensor confirms that the robotic arm has engaged or is in close proximity with a probe. As an example, a Hall effect sensor can be used in conjunction with a permanent magnet to affect the sensors output. In some embodiments, a Hall effect sensor is noise immune, non-contact, and has a consistent detection range. Any of a number of different types of Hall sensors may be utilized, and in many cases, the sensor functions as a simple switch and linear range measurement and detection in which the overall output voltage is set by the supply voltage and varies in proportion to the strength of the magnetic field. This results in a distance measurement between the sensor and a locating magnet and may be used to measure the distance between the robotic arm and the probe and aid in docking. The sensor and beacon may be located within respective housings of the robotic arm and probe.

In some embodiments, positional sensing of the robotic arm is performed by an inertial measurement unit (IMU), which may include up to 9-axis detection. In some cases, a 6-axis IMU can be used for motion detection, vibration detection, positional orientation information, redundancy and backup of the primary encoder signals that may be located in the joints of the robotic arms. The IMUs may perform a dual function of seeking a probe for docking with the robotic arm as well as force detection and motion compensation as described herein. The described sensors can be used in combination with any robotic arms or probes described herein.

According to some embodiments, the procedure for docking a robotic arm with a probe may comprise an IR beacon to provide coarse positional and spatial location for homing detection, fiducials on either the arm or the probe and an optical sensor to view the fiducials which can be used to allow fine alignment of positional location in the XY plane, and a Hall effect sensor to detect Z direction proximity for docking. An IR beacon allows for larger distance seek for the home position of the robotic arm relative to the probe. The fiducials and optical sensor may allow for rapid, low-latency detection of the 2D location and 2D orientation of the probe by the robotic arm. A user interface, which may be located on the robotic arm, on the probe, or on a robotic arm control unit, may indicate distance, position, docked status or other information. In some embodiments, the user interface includes one or more visual cues, such as LED indicators, to indicate the relative position and/or docking status of the arm and probe.

While the coupling mechanism shown in FIGS. 5A and 5B is described in the context of coupling the treatment probe to the first robotic arm, a substantially similar mechanism may also be used for coupling the imaging probe to the second robotic arm 444. For example, the coupling structure of the second robotic arm 444 may comprise a similar coupling mechanism for engaging an attachment device connected to the imaging probe.

Figure 6A:
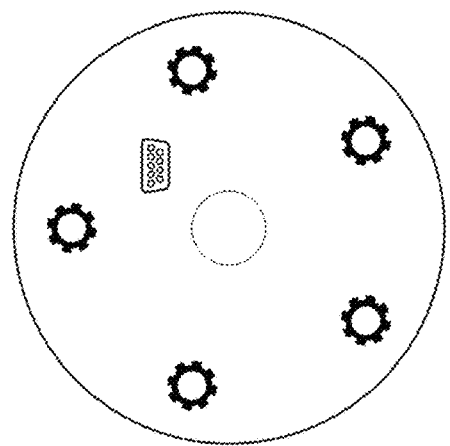
FIG. 6A schematically shows an exemplary end of an instrument device manipulator, having 5 linkages and an electrical port, in accordance with some embodiments.
Figure 6B:
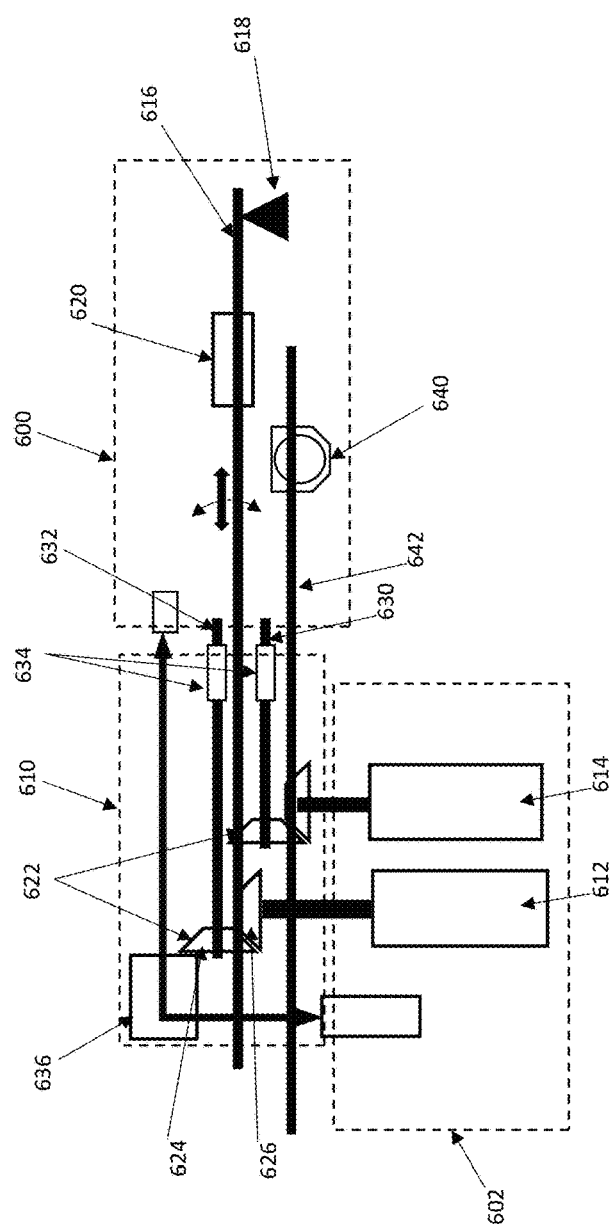
FIG. 6B schematically illustrates a system for coupling a handpiece to an instrument device manipulator by way of a right-angled shaft transmission, in accordance with some embodiments.
Figure 6C:
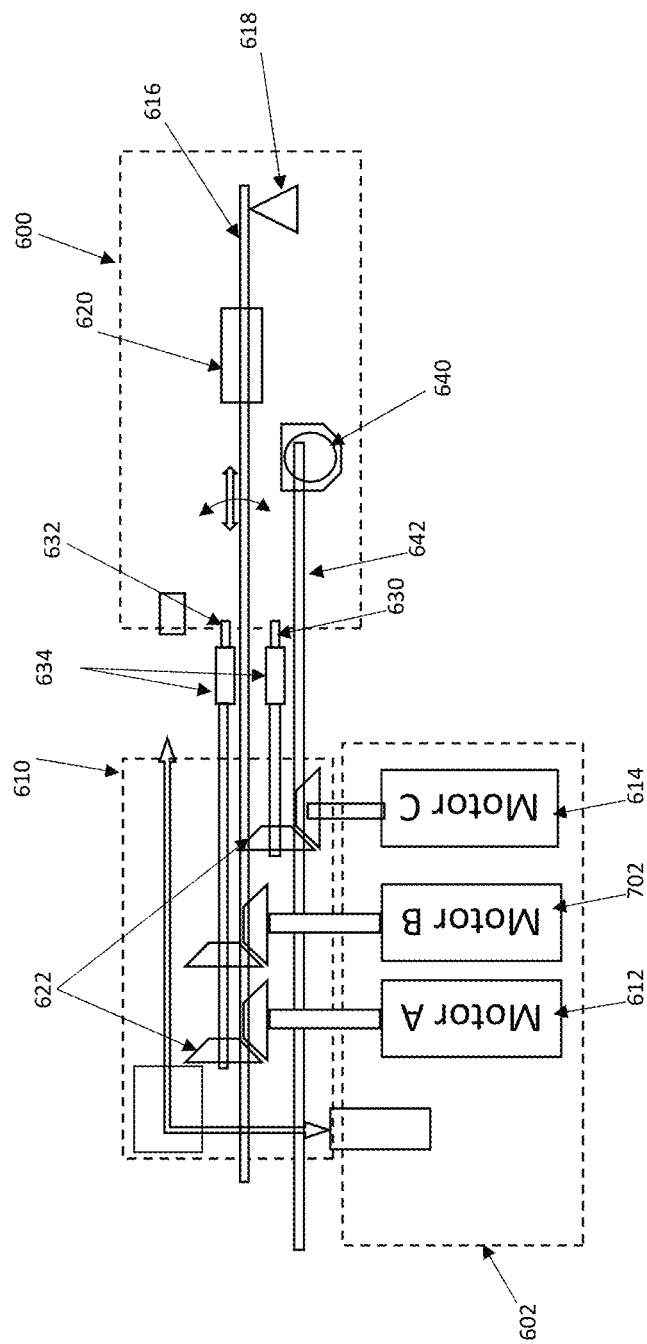
FIG. 6C schematically illustrates a system for coupling a handpiece to an instrument device manipulator by way of a right-angle transmission, in accordance with some embodiments.

FIGS. 6A-6C show exemplary couplings between a handpiece 600 and an instrument device manipulator 602. Throughout this description of various embodiments, the handpiece 600 may comprise any of a variety of instruments, such as, for example imaging probes, treatment probes, surgical tools, catheters, energy delivery systems, implants, visualization systems, and other instruments that may be desirable to be used during the diagnosis or treatment of a patient. In some embodiments, a handpiece 600 may be similar to the attachment device 500 described herein. As used throughout this description, reference to an instrument device manipulator 602 may refer to a robotic arm. The instrument device manipulator 602 may have one or more motors associated therewith, which may be carried internally or externally to the instrument device manipulator 602. In some embodiments, an instrument device manipulator 602 may carry one, two, three, four, five, six, seven, eight, or more motors. One or more of the motors may have an output shaft that is turned rotationally by the motor. One or more of the motors of the instrument device manipulator 602 may comprise a linkage (e.g., gear) on the output shaft of the motor. The linkage may comprise a pinion gear, a bevel gear, a spur gear, a helicoid gear, a worm drive gear, a planetary gear, or some other type of linkage. The linkage may be coupled to another linkage, a chain, a belt, or some other type of transmission 610 linkage associated with the transmission 610 to transfer the rotational motion of the motor into motion of one or more parts of the handpiece 600. In some cases, the rotational motion of the motor is transferred to rotational motion of a component of the handpiece 600, while in some cases, the rotational output of the motor is transferred to linear motion of a component of the handpiece 600. The following figures provide exemplary systems for coupling an instrument device manipulator 602 to one or more instruments, such as a handpiece 600, a probe, a scope, or other instrument.

FIG. 6A shows an exemplary end 604 of an instrument device manipulator 602, having 5 linkages 606 and an electrical port 608. While the illustrated embodiment shows 5 linkages 606, it should be appreciated that the instrument device manipulator 602 may have any suitable number of linkages 606, such as two, three, four, five, six, seven, eight, nine, or more. While the linkages 606 are shown as gears, any type or combination of suitable linkages 606 may be used. Examples of linkages for rotational motion include, but are not limited to, round shafts with flats, round shafts with keyway slots, square or rectangular shafts, spline couplings, pentagonal shafts, hexagonal shafts, and the like. Linkages 606 may also provide translational motion. The electrical port 608 may provide electrical power and communication to the handpiece 600, such as for allowing signals to pass between the handpiece 600 and a computing device that may implement a treatment plan and control the actuation of the instruments of the handpiece 600.

FIG. 6B shows an exemplary coupling between a handpiece 600 and an instrument device manipulator 602. A transmission 610 couples the handpiece 600 to the instrument device manipulator 602 and transfers the output from one or more motors 612 associated with the instrument device manipulator 602 to the handpiece 600. The transmission 610 may include speed reduction or speed multiplication to couple efficiently between the motor 612 of the instrument device manipulator 602 and the R-drive, Z-drive, or both of the handpiece 600. In some cases, a transmission 610 can be configured to couple several configurations of handpiece 600 to an instrument device manipulator 602. For instance, a transmission 610 can be configured to receive the output from one or more motors 612 associated with the instrument device manipulator 602 and transfer the motion to any of a variety of handpieces 600. In this way, a handpiece 600 does not need to be manufactured to couple with a specific instrument device manipulator 602, but rather, because the transmission 610 can be configured to couple with both, the handpiece 600 and its associated instruments can be manufactured without regard to the instrument device manipulator 602 that it may ultimately be coupled to.

The handpiece 600 may comprise any suitable treatment probe 616, such as a waterjet 618 for example, and is coupled to the instrument device manipulator 602 with an attachment device which may comprise a reusable transmission 610. A reusable transmission 610 may offer advantages as mechanical and electrical precision can be built into the device with a minimal impact on the cost of a single procedure. The handpiece 600 may be removably coupled to the transmission 610 and the transmission 610 may be removably coupled to the instrument device manipulator 602. Removable couplings promote interchangeability of similar devices and give the surgeon the ability to quickly and easily change between instruments of different types in response to medical imperatives. The handpiece 600 may comprise a position encoder 620 that is configured to send a signal associated with the position of the treatment probe 616. The signal may correspond to the rotation angle, position, orientation, translation, or a combination of the treatment probe 616. Additional encoders 620 may be provided to send signals associated with the position or orientation of other instruments, such as an imaging probe, endoscope, catheter, laser, microwave, and others. Similarly, one or more encoders may be provided in conjunction with the instrument device manipulator 602 to determine the position and orientation of the instrument device manipulator 602.

The transmission 610 may comprise a connector configured to couple the instrument device manipulator 602 to lock the transmission 610 in place to the instrument device manipulator 602. The instrument device manipulator 602 may comprise a coupling structure disposed at the distal end of the arm, configured to rigidly receive the connector of the transmission 610. Similarly, an additional coupling structure may be provided between the transmission 610 and the handpiece 600. Once the handpiece 600 and the instrument device manipulator 602 are coupled together by the transmission 610, movement of the handpiece 600 may be controlled by moving the instrument device manipulator 602 (e.g., by articulating one or more joints of the instrument device manipulator 602 under computer control, or under manual control, or actuating one or more motors of the instrument device manipulator 602).

In some embodiments, the handpiece 600 is coupled to the transmission 610 by a quick release mechanism, such that the coupling between the handpiece 600 and the transmission 610 is capable of a quick disconnect in order to prevent injury to the patient in case the instrument device manipulator 602 loses position or otherwise fails to operate correctly. The quick release mechanism may also facilitate changing handpiece 600s and instruments quickly, even during a procedure where it is desirable to attach alternative instruments to the instrument device manipulator 602.

Similarly, the transmission 610 may be coupled to the instrument device manipulator 602 through a similar mechanism, which may provide for a quick release. The coupling of the handpiece 600 to the transmission 610 and the transmission 610 to the instrument device manipulator 602 may be carried out by a similar connecting structure or may be different structures. For instance, the handpiece 600 may couple to the transmission 610 by a magnetic coupling while the transmission 610 may couple to the instrument device manipulator 602 by a mechanical locking structure. Other coupling structures may include a slot having a magnet disposed therein and a cooperating ferromagnetic fixture can be configured to fit in the slot. The couplings may be provided by a latching mechanism to selectively engage or disengage the cooperating coupling member. Further, the coupling structure may comprise a rotating knob, a lever, a cooperating boss and pocket, a hook, a latch, or some other suitable type of connector to releasably secure the handpiece 600 to the transmission 610 and the transmission 610 to the instrument device manipulator 602.

As illustrated, the instrument device manipulator 602 may have two motors 612. The right-angle transmission linkages 622 shown in FIG. 6B may be preferable geometrically in some cases pertaining to the arrangement of the linkages of the arm which supports the instrument device manipulator 602. A first motor 612 has an output shaft carrying a linkage, such a bevel gear, a worm gear, a helicoid gear or some other configuration. The first motor 612 is coupled to a cooperating linkage of the transmission 610. The transmission 610, in turn, is coupled to an instrument, such as a waterjet 618, and provides for rotational motion of the instrument. In some embodiments, the instrument comprises a distal end and a proximal end, and a lumen extending between the distal end and the proximal end. The distal end may carry an energy source such as a nozzle, and the proximal end may be coupled to a source of high-pressure fluid. In some cases, the instrument is maintained substantially straight as it is carried by the transmission 610. In some cases, the instrument fits within a groove formed on the outside of the transmission 610 to facilitate quick insertion and removal of the instrument with the transmission 610. The instrument may be retained by a retaining structure carried by the transmission 610, such as a clip, a lever, or some other suitable structure.

A second motor 614 of the instrument device manipulator 602 has an output shaft that carries a linkage, which may be a bevel gear 622, a worm drive, a helicoid gear, or some other suitable gear. The second motor 614 is coupled to a cooperating gear of the transmission 610. The transmission 610 is, in turn, coupled to an instrument, such as the waterjet 618, and is used to provide translational linear motion of the instrument. In some instances, the transmission 610 comprises a step-up transmission 610, in which the rotational output of the transmission 610 is faster than the rotational input of the transmission 610. This may be accomplished, for example, by a driven gear 624 having a smaller pitch circle than a driving gear 626. In some embodiments, the driven gear 624 has a smaller number of gear teeth compared to the driving gear 626. Alternatively, the transmission 610 may be step-down transmission 610, in which a driven gear 624 has a larger pitch circle than a meshed driving gear 626. In such cases, the driven gear 624 may have more teeth than the driving gear 626 which causes it to rotate slower than the driving gear 626.

In some embodiments, the first motor 612 and the second motor 614 of the instrument device manipulator 602 are coupled to a single input of the transmission 610. For example, two or more motors of the instrument device manipulator 602 may be coupled together within the transmission 610 to combine their power into a single output shaft. Additionally, the transmission 610 may take the two or more motors and through gearing or other leveraging mechanics, cause the output shaft to step down the input from the two or more motors to result in greater combined torque, or step up the input from the two or more motors to result in greater speed. A step-down transmission 610 may be useful where torque is preferred to speed, such as for applying a clamping force. A step-up transmission 610 may be useful where speed is preferred over torque, such as for ultrasonic motion, burr cutting, friction heating, or other suitable high-speed process.

The transmission 610 may comprise a right-angle transmission 610 wherein the output shafts of the instrument device manipulator 602 motors is orthogonal (or substantially orthogonal) to the input shafts of the handpiece 600. For expediency in describing the various configurations, the handpiece 600 has a longitudinal axis and the treatment probe 616 (e.g., water jet) runs parallel to the longitudinal axis of the handpiece 600, which is also referred to as the Z-direction. An X-Y plane is orthogonal to the Z-direction. In some embodiments, the water jet is translated in the Z-direction by the second motor, also referred to as a Z-drive 630, and is rotated about its longitudinal axis by a rotational motor ("R-drive") 632. The treatment probe 616 translates longitudinally and/or oscillates rotationally under instructions by a computing device. The computing device sends signals to the instrument device manipulator 602 to actuate one or more motors 612 that are coupled to the instruments of the handpiece 600 by linkages. The handpiece 600 has one or more encoders 620 that send signals back to the computing device, such as location, position, orientation, translation, or some other signal indicative of a parameter of the handpiece 600, or one or more instruments of the handpiece 600.

The handpiece 600 may couple to the transmission 610 in such a way as to mechanically couple the R-drive 632 and the Z-drive 630 with the instruments of the handpiece 600. For example, the transmission 610 may include a coupler 634, such as a hex-shaft coupler, that receives a corresponding shaped structure of the handpiece 600, such that when the handpiece 600 is coupled to the transmission 610, the instruments of the handpiece 600 are in driving engagement with the transmission 610. Other couplers are contemplated, and include, without limitation, round couplers with flats, round couplers with keyway slots, square or rectangular couplers, spline couplers, pentagonal couplers, and the like. Accordingly, the motors of the instrument device manipulator 602 are coupled to the transmission 610, which transfers the motion of the instrument device manipulator 602 motors to the instruments of the handpiece 600. Once coupled, activation of the instrument device manipulator 602 motors results in R-drive or Z-drive motion of the instruments of the handpiece 600.

In some embodiments, an input from the instrument device manipulator 602 may provide for articulation of one or more instrument of the handpiece 600. For example, an instrument, such as a probe, scope, or other device, may be flexible, have segments, joints, or have other ways of allowing articulation of the instrument. An input from the instrument device manipulator 602 may be used to articulate the instrument, such as, for example, by manipulating a wire, such as by tensioning, twisting, compressing, or some other applied force. Instruments of the handpiece 600 may be rotated, translated, articulated, or a combination of movements in response to applied forces from the instrument device manipulator 602.

An electrical system interface device 636 may be carried by the transmission 610 and can transmit, condition, or interpret electrical signals between the instrument device manipulator 602 and the handpiece 600. The electrical system interface device 636 may include one or more electrical connectors to electrically couple the handpiece 600 and the instrument device manipulator 602 when the handpiece 600 is coupled to the instrument device manipulator 602 by the transmission 610. The electrical system interface device 636 may send electrical power and/or commands to the handpiece 600, such as from a computing system, and may send signals from the handpiece 600 to the instrument device manipulator 602, such as signals associated with force, imaging, volume, position, direction, orientation, temperature, or some other parameter. It may also provide signal processing between the handpiece 600 and the instrument device manipulator 602, as well as signals passing to and from system 400. In some embodiments, the handpiece 600 comprises one or more encoders 620 for sending a signal associated with a parameter of the handpiece 600 to the computing system.

An imaging device, such as a cystoscope 642, ultrasound probe, or other type of imaging device, may be carried by the handpiece 600, and may be manually positioned by a manual position control device 640.

FIG. 6C illustrates a system for coupling a handpiece 600 to an instrument device manipulator 602 by a right-angle shaft transmission 610. As illustrated, the transmission 610 may utilize 2 R-drive motors 612, 702 for rotational motion, such as for driving an instrument (e.g., a water jet) rotationally about its longitudinal axis. The handpiece 600 may be as substantially described elsewhere herein and the instrument device manipulator 602 may likewise be as substantially described herein, such as in relation to FIGS. 2-6B. The instrument device manipulator 602 may have three or more motors that mechanically couple to the transmission 610. For example, the transmission 610 may receive the input from two motors 612, 702 and transmit the input into rotational motion of an instrument, such as a treatment probe 616, such as a waterjet, for example. A third motor of the instrument device manipulator 602 may provide an input to the transmission 610 that is coupled to the handpiece 600 to provide linear motion in a Z-direction, as illustrated. In the illustrated embodiment, the imaging device (e.g., cystoscope), may be manually driven in a rotational direction, a Z-direction, or in some other direction.

Figure 7A:
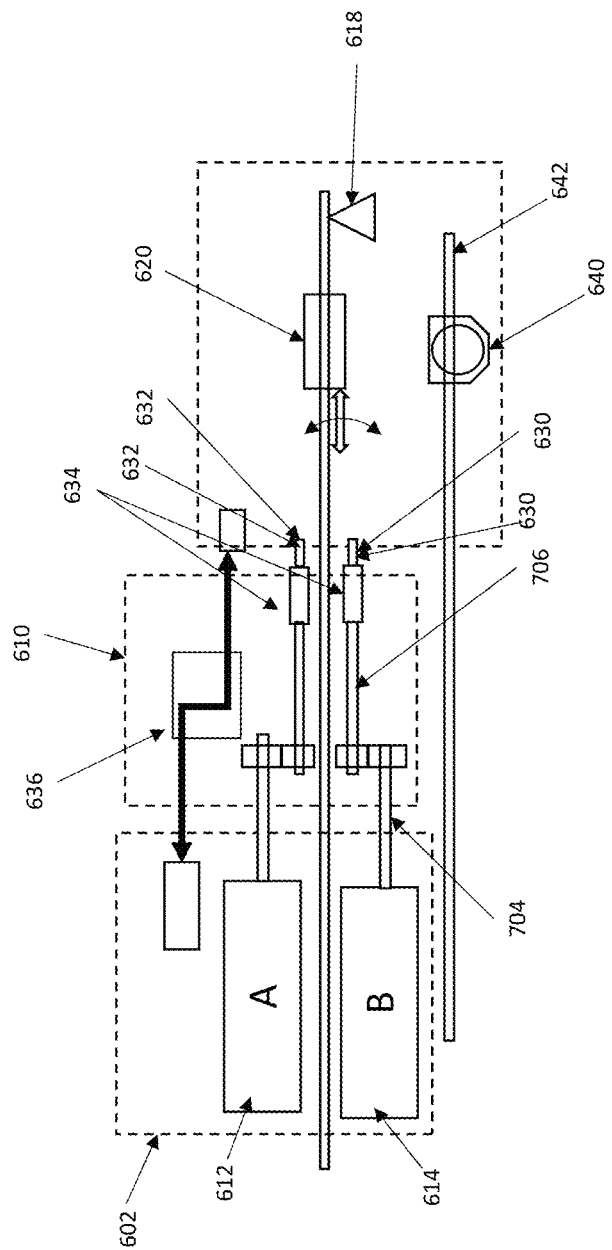
FIG. 7A schematically illustrates a system for coupling a handpiece to an instrument device manipulator by a parallel shaft transmission, in accordance with some embodiments.

FIG. 7A illustrates a system for coupling a handpiece 600 to an instrument device manipulator 602 by a parallel shaft transmission 610. The parallel-shaft transmission 610 linkages shown in FIG. 7A may be preferable geometrically in certain cases pertaining to the arrangement of the linkages of the arm which supports the instrument device manipulator 602. The handpiece 600 may be as substantially described elsewhere herein and the instrument device manipulator 602 may likewise be as substantially described herein, such as in relation to FIGS. 2-6C. An instrument device manipulator 602 may have two motors 612, 614 that mechanically couple to the transmission 610, as described herein. In turn, the transmission 610 can mechanically couple to the handpiece 600 and any instruments associated with the handpiece 600.

In some embodiments, a single instrument device manipulator 602 has two or more motors. A first motor 612 is coupled to the handpiece 600 through the transmission 610 to provide an R-drive 632 for an instrument, such as a waterjet 618. A second motor 614 is coupled to the handpiece 600 through the transmission 610 to provide Z-drive 630 of an instrument, such as the waterjet. The transmission 610 receives input shafts from the instrument device manipulator 602 and comprises output shafts that provide a driving engagement to the instruments of the handpiece 600. The transmission 610 may comprise a parallel transmission 610, in which the input shafts 704 and output shafts 706 are substantially parallel. The input shafts 704 can be coupled to the output shafts through any suitable structure, such as cooperating gears, a belt, a link, a chain, or some other linkage that couples the input shafts to the output shafts 706.

The transmission 610 may comprise an electrical system interface device 636 that provides electrical communication between the instrument device manipulator 602 and the handpiece 600, as described herein. The electrical system interface device 636 may comprise one or more electrical couplers that allow electrical communication between the instrument device manipulator 602 and the handpiece 600, such as for power and delivering unidirectional or bidirectional electrical signals. It may also provide signal processing between the handpiece 600 and the instrument device manipulator 602, as well as signals passing to and from system 400.

The handpiece 600 may comprise any of a number of instruments, such as a waterjet 618, as illustrated. The first motor 612 of the instrument device manipulator 602 may be coupled to provide an R-drive 632 to the waterjet, and the second motor 614 of the instrument device manipulator 602 may be coupled to provide a Z-drive 630 to the waterjet. While a waterjet is used throughout as an exemplary instrument of the handpiece 600 that is operated by motors associated with the instrument device manipulator 602, it should be appreciated that many other types of instruments (e.g., laser, microwave, transducer, etc.) could likewise be manipulated in the same, or a similar manner, and the description of a waterjet in conjunction with embodiments described herein should not be limiting.

An imaging device may be associated with the handpiece 600 and may be positioned by a manual position control device 640. The manual position control device 640 may be any suitable device, but in some embodiments, comprises a knob, a wheel, a handle, a cam, a gear, or some other structure that allows selective positioning and locking of the imaging device with respect to the handpiece 600.

Figure 7B:
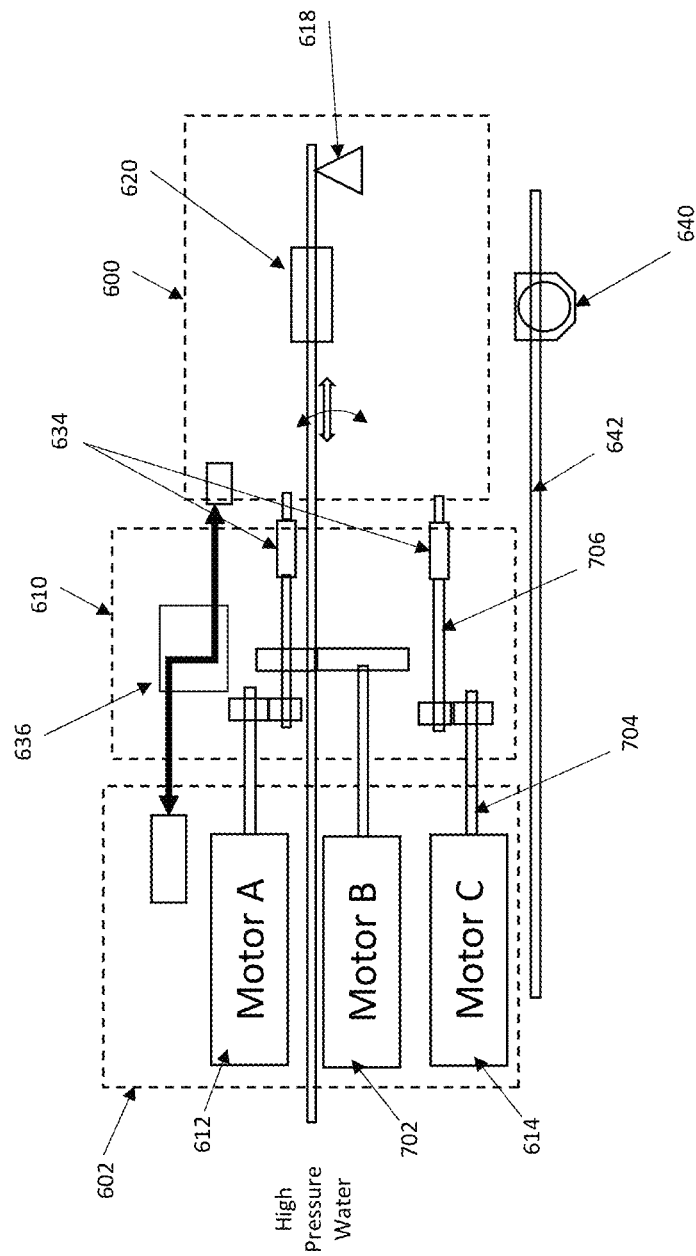

FIG. 7B illustrates a system for coupling a handpiece 600 to an instrument device manipulator 602 by a parallel-shaft transmission 610. The parallel-shaft transmission 610 linkages shown in FIG. 7B may be preferable geometrically in certain cases pertaining to the arrangement of the linkages of the arm which supports the instrument device manipulator 602. The handpiece 600 may be as substantially described elsewhere herein and the instrument device manipulator 602 may likewise be as substantially described herein, such as in relation to FIGS. 2-6C. An instrument device manipulator 602 may have three motors that mechanically couple to the transmission 610, as described herein. In turn, the transmission 610 can mechanically couple to the handpiece 600 and any instruments associated with the handpiece 600.

As an example, two motors of the instrument device manipulator 602 may be coupled to the handpiece 600 and provide for rotational motion of an instrument of the handpiece 600. The two motors may operate in opposite directions and selectively drive the instrument in two rotational directions. A third motor 702 may drive the handpiece 600, or an instrument of the handpiece 600, in a Z-direction. The motors may engage the transmission 610 through any suitable mechanism, as described elsewhere herein, and the output from the motors of the instrument device manipulator 602 can be transmitted to the handpiece 600, one or more instruments of the handpiece 600, or other devices useful in a medical procedure.

FIG. 8 illustrates a system for coupling a handpiece 600 to an instrument device manipulator 602 by a right-angled shaft transmission 610 with a motorized imaging probe 806. The handpiece 600 and instrument device manipulator 602 may be as substantially described elsewhere herein, such as in relation to FIGS. 2-6C, among others. The instrument device manipulator 602 may comprise three motors that operatively couple to the transmission 610. The transmission 610 may comprise a right-angle shaft transmission 610 and corresponding gears may change the direction of the output shaft relative to the input shaft.

In some embodiments, the transmission 610 includes a gear having internal teeth that receive the external teeth of a motor gear. In other words, a transmission 610 gear may surround the motor gear as the transmission 610 is coupled to the instrument device manipulator 602. The transmission 610 gear may then couple with another gear to facilitate the right-angle shaft transmission 610 configuration.

A second motor 614 of the instrument device manipulator 602 may couple to a second linkage of the transmission 610 to provide a Z-drive for one or more instruments of the handpiece 600. A third motor 802 of the instrument device manipulator 602 may couple to a third linkage 804 of the transmission 610 to provide a Z-drive of the imaging device 806. The imaging device 806 may be driven by any suitable mechanism that converts rotary motion of the motor 802 to linear motion of the imaging device 806, such as a rack and pinion, a belt drive, a chain drive, a worm drive, or some other mechanism.

FIG. 9 illustrates a system for coupling a handpiece 600 to an instrument device manipulator 602 by a parallel shaft transmission 610 with a motorized imaging device 806. The handpiece 600 and instrument device manipulator 602 may be as substantially described elsewhere herein, such as in relation to FIGS. 2-6C, among others. The embodiment of FIG. 9 may also be substantially similar to that of FIG. 8; however, FIG. 9 shows a parallel shaft transmission 610 as opposed to the right-angle shaft transmission 610 of FIG. 8. The parallel shaft transmission 610 can be as described elsewhere herein and use any combination of linkages or other suitable structure to transfer the output from the instrument device manipulator 602 motors to instruments of the handpiece 600.

According to some embodiments, a pressure regulating valve 902 may be provided to control, vary, or regulate the pressure of the waterjet 618. In some cases, the pressure regulating valve 902 comprises a throttling valve, a pressure relief valve, or some other suitable mechanism for varying the pressure of the water delivered to the waterjet 618. The pressure of the waterjet 618 may be controlled in response to an angle of the waterjet 618. For example, as the waterjet 618 is rotated, the water pressure may be higher at some predetermined angular orientations and lower at other predetermined orientations. The tissue treatment profile may indicate a cut profile of tissue to be treated, and in some cases, the depth of cut varies along the tissue treatment profile. In these cases, the pressure of the waterjet 618 may be varied in order to affect the tissue treatment profile. In other words, the water pressure may be dynamically varied along the cut profile to achieve the desired cut profile.

In some cases, the cut profile, in a rotational direction relative to the waterjet 618, may resemble an ellipse, or a partial ellipse. The pressure of the waterjet 618 may be dynamically controlled to achieve this cut profile. The pressure of the waterjet may be dynamically controlled in any suitable way, and in some cases, is controlled by one or more valves 902 (e.g., throttling valve, pressure relief valve, pressure control valve), in other cases, the pressure may be controlled by a pump that is driven to achieve variable water pressures that achieve the cut profile in combination with the waterjet being moved according to the treatment plan. The water pressure may thus be varied quickly as the waterjet instrument translates, rotates, and/or oscillates.

FIG. 10 illustrates a system for coupling a handpiece 600 to an instrument device manipulator 602 by a right-angle shaft transmission 610 providing for 2 rotational motors to be coupled to a surgical instrument. The handpiece 600 and instrument device manipulator 602 may be as substantially described elsewhere herein, such as in relation to FIGS. 2-6C, among others. The instrument device manipulator 602 may comprise three or more motors that are in driving engagement to the transmission 610 once the transmission 610 is coupled to the instrument device manipulator 602. Two motors 614, 702 may be used as R-drive motors, with each R-drive motor operating in one rotational direction, the two motors operating in opposite rotational directions. The use of two motors in opposition may promote rapid reversal of the direction of rotation, leading to more accurate positioning of the water jet and faster tissue resection. Use of two motors may also promote improved longevity of the device by way of reducing the duty cycle on individual motors, thus allowing the internal wiring of each motor to operate at lower temperatures.

A clutch 1002 may be disposed on the transmission shaft that selectively couples and decouples one or more of the R-drive motors 614, 702. A second clutch 1004 may optionally be provided, and each clutch may be configured to selectively couple and decouple an associated R-drive motor 614, 702. The one or more clutches may be electrically actuated to alternatively couple and decouple the R-drive motors such that only one Z-drive motor is coupled to the treatment probe 616 at any one time.

In some instances, a rotary inertia flywheel 1006 may be carried by the R-drive motor output shaft. The rotary inertia flywheel 1006 may be used to increase the rotational inertia of the R-drive motor such that the rotational inertia of the R-drive motor is substantially higher than the rotational inertia of the rotating treatment probe 616 (e.g., a water jet). In some embodiments, the R-drive motors only spin in one direction, in order to quickly change the rotational direction of the treatment probe 616, increasing the rotational inertia of the R-drive motors provides for quick reversal of the rotational direction of the treatment probe 616. In some instances, the R-drive motors are configured to rotate the treatment probe 616 at a rate of up to 10 revolutions per second (rps) (3600° per second). In some embodiments, the treatment probe 616 may rotate in an arc of from about 5° to about 235°, and may be configured to rotate in an arc of 15°, or 30°, or 45°, or 60°, or 90°, or 120°, or 225°, or any arc as determined by the anatomy of the patient and the treatment plan established by the surgeon. In some instances where the treatment arc is 60°, the treatment probe 616 may change direction about twelve times per second. This may cause significant torsional stress on the treatment probe 616 shaft. In some embodiments, one or more torsional shock springs 1008 are provided to absorb at least some of the torsional stress caused by rapid direction changes.

The transmission 610 may carry an electrical system interface device 636, as described herein, and carry signals that operate the one or more clutches to engage and disengage the R-drive motors according to a treatment plan. In some cases, the treatment plan defines a volume of resection and the waterjet 618 is driven rotationally in a sweeping arc according to the treatment plan in order to remove the appropriate volume of tissue. The electrical system interface device 636 may carry a signal, such as from a computer that issues instructions according to the treatment plan, to control the rotational speed of the R-drive motors 612, 702 and the clutch timing to provide treatment to the desired volume of tissue.

A Z-drive motor 614 may position the handpiece 600 in the Z-direction according to the treatment plan. By operating the two R-drive motors and the Z-drive motors in concert, the waterjet may be configured to oscillate and translate at a desired speed to treat a predetermined volume of tissue. In some cases, the Z-drive provides a rapid motion in the Z-direction. For example, the Z-drive 630 may move the waterjet 618 at speeds of 30 cm per second, which is the equivalent of a jet rotating at 720° per second at a predetermined cutting depth. In some embodiments, one or more optical encoders 620 are used to sense the rotational travel limits of the waterjet and send a signal to reverse the direction of rotation of the waterjet 618.

FIG. 11 illustrates a system for coupling a handpiece 600 to an instrument device manipulator 602 by a parallel shaft transmission 610 providing for 2 rotation motors coupled to a surgical instrument. The handpiece 600 and instrument device manipulator 602 may be as substantially described elsewhere herein, such as in relation to FIGS. 2-6C, among others. The illustrated embodiment of the transmission 610 may be substantially similar to the embodiments illustrated in FIG. 10; however, a parallel shaft transmission 610 shown as opposed to the right-angle transmission 610 of FIG. 10.

FIG. 12 illustrates a system for coupling a handpiece 600 to an instrument device manipulator 602 by a right-angle shaft transmission 610 providing for two rotation motors coupled to a surgical instrument and a motorized scope 806. The handpiece 600 and instrument device manipulator 602 may be as substantially described elsewhere herein, such as in relation to FIGS. 2-6C, among others. The illustrated embodiment may be similar to the embodiments of FIG. 10, with the addition of a fourth Z-drive motor 1202 coupled to the imaging device 806 (e.g., cystoscope) to allow computer control of the position of the imaging device 806 in the Z-direction.

FIG. 13 illustrates a system for coupling a handpiece 600 to an instrument device manipulator 602 by a parallel shaft transmission 610 providing for two rotation motors coupled to a surgical instrument (e.g., treatment probe 616) with a motorized imaging probe 806. The handpiece 600 and instrument device manipulator 602 may be as substantially described elsewhere herein, such as in relation to FIGS. 2-6C, among others. The illustrated embodiments may be similar to those of FIG. 12 with the substitution of a parallel shaft transmission 610 in place of the right-angle shaft transmission 610.

FIG. 14 illustrates a system for coupling a handpiece 600 to an instrument motor driver 1402 providing for 2 rotation motors. In some embodiments, a handpiece 600 is coupled to an instrument motor driver 1402 by a transmission 610. The instrument motor driver 1402 may be coupled to an instrument device manipulator 602. The handpiece 600 and instrument device manipulator 602 may be as substantially described elsewhere herein, such as in relation to FIGS. 2-6C, among others. In some instances, an instrument device manipulator 602 may not possess motors that can be coupled to actuate the instruments of the handpiece 600. Therefore, in some embodiments, the handpiece 600 is coupled to the transmission 610, which in turn, is coupled to an instrument motor driver. The instrument motor driver 1402 may have two or more motors, such as three, four, five, six, seven, eight, or more motors. The instrument motor driver 1402 is coupled to the transmission 610 by any suitable structure and may be similar to how the transmission 610 can be coupled to an instrument device manipulator 602, as described elsewhere herein.

As illustrated, the instrument motor driver 1402 comprises two R-drive motors 1404, 1406 that may be operated in opposite directions. One or more clutches 1002, 1004 may be selectively engaged and disengaged to allow each R-drive motor to engage with the handpiece 600 in succession to allow rotation of the treatment probe 616 in both rotational directions. Another motor of the instrument motor driver 1402 may be coupled to the handpiece 600 to provide Z-direction linear motion. Other motors of the instrument motor driver may be used for other tasks, for example, for Z-direction translation of an imaging probe, for X-Y linear movement of the handpiece 600, or some other purpose.

The transmission 610 may include one or more torsional shock springs 1008 to reduce the torsional stress that would otherwise be imparted to the treatment probe 616 from oscillating back and forth in response to the R-drive motors engaging and disengaging.

In some cases, the instrument motor driver 1402 is configured to rotationally drive the treatment probe 616, and motors associated with an instrument device manipulator 602 (e.g., robotic arm) are used to manipulate the handpiece 600 and its instruments in X, Y, and Z directions. In some cases, the instrument motor driver 1402 comprises one or more R-drive motors 1404, 1406 for rotating the treatment probe 616, while the instrument device manipulator 602 includes one or more motors for driving the treatment probe 616 in a Z-direction, and optionally, other instruments of the handpiece 600 in X,Y, and/or Z directions.

FIG. 15 illustrates a system for coupling a handpiece 600 to an instrument motor driver 1402 providing for 2 rotation motors 1404, 1406 that provide rapid motor direction switching. The illustrated instrument motor driver 1402 and handpiece 600 may be substantially similar to other embodiments described herein.

The instrument motor driver 1402 may be coupled to an instrument device manipulator 602, as previously described. The transmission 610 couples the handpiece 600 and the instrument motor driver 1402 to transmit rotational motion from the instrument motor driver 1402 to linear and/or rotational movement of the handpiece 600 or instruments of the handpiece 600. The transmission 610 may include a linkage 606 for operatively coupling the output shafts of motors associated with the instrument motor driver 1402 with instruments of the handpiece 600. In some cases, the linkage 606 comprises a gear, a chain, a belt, or some other linkage 606. The instrument motor driver 1402 may have two motors configured to drive the treatment probe 616 in a rotational direction and the two R-drive motors may rotate in opposite directions. Each R-drive motor may fluctuate between periods of driving and being driven in opposition to the other R-drive motor. The actuation of the two R-drive motors may be timed such that one motor is driving while the other motor is idle. To change direction, the two motors switch states. In this way, only one motor is actively driving the treatment probe 616 at a time. As the R-drive motors are driven sequentially, the treatment probe 616 oscillates about its longitudinal axis in response to being driven by the motors in sequence in opposite directions. The motors may be controlled by a computing device and driven to oscillate the treatment probe 616 according to a treatment plan.

FIG. 15 further shows a timing diagram of the R-drive motors 1404, 1406 as they are driven in sequence. One or more electronic modulators may be responsible for driving the two R-drive motors sequentially.

In practice, it has been observed that there is a large amount of back electromotive force (EMF) generated when driving the motors quickly and reversing the direction of the motors. The generated back EMF acts against the applied voltage that is causing the motor to spin and reduces the current flowing through the coils of the motor. By turning off the motors in sequence, the back-EMF is largely isolated when the motor is allowed to idle, thus increasing the efficiency of the system.

In some embodiments, the motors may be selectively coupled to the treatment probe 616 by the transmission 610, and in some embodiments, as one R-drive motor is engaged with the treatment probe 616, the other motor idles or is otherwise disengaged from driving the treatment probe 616. The R-drive motors can sequentially engage and disengage from the treatment probe 616 in sequence such that the treatment probe 616 oscillates in the R-direction according to the treatment plan. The oscillation may be performed, for example, by including gear teeth around only a portion of the driving gear of the R-drive motor. For example, the driving gear of each R-drive motor may include gear teeth around discrete portions of its circular pitch. As an example, the driving gears may include teeth for 30°, and then a land for 30°, followed by teeth for 30° and a land for 30°. The gears may be arranged so that only one gear drives the treatment probe 616 at a time which oscillates the probe in an R-direction.

FIG. 16 illustrates a system for coupling a handpiece 600 to an instrument device manipulator 602 by a parallel shaft transmission 610 providing for 2 rotation motors. The handpiece 600 and instrument device manipulator 602 may be as substantially described elsewhere herein, such as in relation to FIGS. 2-6C, among others. As illustrated, two R-drive motors 612, 702 of the instrument device manipulator 602 are coupled to the transmission 610 to provide oscillating rotation to the treatment probe 616 (e.g., water jet). The R-drive motors may optionally comprise flywheels 1006 to increase the rotational inertia of the R-drive motors. The transmission 610 may comprise one or more torsional springs 1008 to reduce the torsional stress on the treatment probe 616 as it oscillates. A Z-drive motor 614 may be coupled to the treatment probe 616 to linearly translate the treatment probe 616 according to the treatment plan.

A fixation structure 1602 may couple the handpiece 600 to the transmission 610 and further provide support for an imaging probe 806, such as a cystoscope, a TRUS probe, or some other device. The imaging probe 806 may be manually positioned in a Z-direction or may be driven by a motor associated with the instrument device manipulator 602. An electrical system interface device 636 may be provided, which may be substantially as described elsewhere herein for providing electrical communication to and from the handpiece 600.

FIG. 17 illustrates a system for coupling a handpiece 600 with two instrument device manipulators 602 and a driven imaging probe 616. The handpiece 600 and instrument device manipulators 602, 1704 may be as substantially described elsewhere herein, such as in relation to FIGS. 2-6C, among others. A first transmission 610 may be coupled to a first instrument device manipulator 602 and the handpiece 600. The first transmission 610 may provide for R-drive of the handpiece 600 instruments and/or Z-drive of the handpiece 600 instruments.

A second transmission 1702 may be coupled to a second instrument device manipulator 1704 and the handpiece 600. The second transmission 1702 may allow a motor associated with the second instrument device manipulator 1704 to provide motion to instruments of the handpiece 600. As shown, the second instrument device manipulator 1704 provides a rotational input from a motor 1706, which is converted to linear translation by the second transmission 1702 to provide a Z-drive for the imaging probe 806. By this type of arrangement, two instrument device manipulators can be coupled to a single handpiece 600 to operate the various instruments associated with the handpiece 600. In some cases, an instrument device manipulator 602 may not include sufficient motors to actuate all the instruments of the handpiece 600, in this case, two or more instrument device manipulators 602 can cooperate to operate the instruments of the handpiece 600, such as by providing X, Y, and Z positioning of the handpiece 600, as well as R-drive and Z-drive to one or more instruments of the handpiece 600. An electrical system interface device 636 may electrically couple one or more instrument device manipulators 602 with the handpiece 600, such as for providing electrical power and communication capabilities. The first and second transmissions 610, 1702 may comprise right-angle shaft transmissions, parallel shaft transmissions, or a combination of right-angle and parallel shaft transmissions.

FIG. 18 illustrates a system for coupling a handpiece 600 with two instrument device manipulators 602 1704 with a right-angle shaft transmission 610 and an imaging probe 806 (e.g., cystoscope) actuated by one instrument device manipulator 602. The embodiments illustrated in FIG. 18 may be substantially similar to those illustrated in FIG. 17, except that FIG. 18 may include an imaging probe 806 that is fixed to an instrument device manipulator 1704 and its position may be directly associated with the position of the instrument device manipulator 1704.

FIG. 19 illustrates a system for coupling a handpiece 600 with two instrument device manipulators 602, 1704 with a right-angle transmission 610 coupled to one instrument device manipulator 602 for controlling the handpiece 600, and a second instrument device manipulator 1704 for controlling a second treatment probe 1710. The handpiece 600 and instrument device manipulators 602, 1704 may be as substantially described elsewhere herein, such as in relation to FIGS. 2-6C, among others. A first instrument device manipulator 602 may have any number of motors for actuating instruments of the handpiece 600. As illustrated, three motors are coupled to the handpiece 600 by a first transmission 610. The first transmission 610 provides for a first motor 612 to provide R-drive to the treatment probe 616, a second motor 614 to provide Z-drive to the treatment probe 616, and a third motor 712 to provide Z-drive to an imaging probe 806.

A second instrument device manipulator 1704 may be coupled to a second transmission 1702 that engages with the handpiece 600. The second instrument device manipulator 1704 may comprise a first motor 1902 that provides an R-drive for a second treatment probe 1710 of the handpiece 600, and a second motor 1706 that provides a Z-drive for the second treatment probe 1710. The second treatment probe 1710 may be used for any purpose, such as for imaging, delivering energy, (e.g., fluid energy, light energy, microwave energy, thermal energy), delivering medicament or radiation, or some other purpose. As described previously, an electrical system interface device 636 can provide power and communication with the handpiece 600.

While the illustrated embodiment appears to show two instrument device manipulators 602, 1704 adjacent one another, it should be appreciated that the two instrument device manipulators 602, 1704 can be positioned in any orientation relative to one another. For example, the two instrument device manipulators 602, 1704 may be adjacent to each other, opposing one another, orthogonal to one another, or some other orientation in order to engage with the transmissions and couple to the handpiece 600. Similarly, the transmissions may be configured with any suitable configuration, such as right-angle shaft transmission, parallel-shaft transmission, direct drive transmission, or some other configuration. Any of the described embodiments may incorporate right-angle shaft transmissions, parallel-shaft transmissions, direct drive transmissions, a combination of transmission types, or some other configuration.

FIG. 20 illustrates a system for coupling a handpiece 600 with two instrument device manipulators 602, 1704, with one instrument device manipulator 602 coupled to the handpiece 600 with a right-angle transmission 610 and another instrument device manipulator 1704 coupled to an imaging probe 806. The handpiece 600 and instrument device manipulators 602 may be as substantially described elsewhere herein, such as in relation to FIGS. 2-6C, among others. As illustrated, a first instrument device manipulator 602 may be coupled to the handpiece 600 by a transmission 610, such as a right-angle transmission 610, and may include one or two R-drive motors, a Z-drive motor coupled to the treatment probe 616, and a Z-drive motor coupled to an imaging probe 806.

A second instrument device manipulator 602 may be coupled to an imaging probe 2002, such as a TRUS probe. The TRUS probe 2002 may be directly coupled to the instrument device manipulator 1704 or may be coupled to a transmission and driven in the Z-direction by a Z-drive motor of the second instrument device manipulator 1704. Similarly, the TRUS probe 2002 may be driven rotationally, and also pivot about an axis in the X or Y directions. The TRUS probe 2002 may have a protective sheath 2004 disposed about its exterior, and the protective sheath 2004 may be coupled to the second instrument device manipulator 1704.

FIG. 21 illustrates a system for coupling a handpiece 600 to an instrument device manipulator 602 by a right-angle transmission 610 and an imaging probe 806 to another instrument device manipulator 1704. The handpiece 600 and instrument device manipulators 602, 1704 may be as substantially described elsewhere herein, such as in relation to FIGS. 2-6C, among others. The first instrument device manipulator 602 may couple to a transmission 610, which is in turn coupled to a handpiece 600. The first instrument device manipulator 602 may comprise three or more motors for actuating instruments of the handpiece 600. For example, a first R-drive motor 612 actuates rotation of the treatment probe 616 of the handpiece 600, a second Z-drive motor 702 actuates linear translation of the treatment probe 616, and a third motor 614 actuates linear translation of an imaging probe 806 of the handpiece 600.

A second instrument device manipulator 1704 may be coupled to a second transmission 1702 and include one or more motors. In some embodiments, the second instrument device manipulator 1704 comprises a first motor 1902 to provide rotation of a second imaging probe 2002 (e.g., TRUS probe), and a second motor 1706 to provide linear translation of the second imaging probe 2002. In some embodiments, the position and orientation of the second imaging probe 2002 may be provided by a direct coupling to the second instrument device manipulator 1704 and the position of the second instrument device manipulator 1704 may determine the orientation and position of the second imaging probe 2002. As previously described, an electrical system interface device 636 can provide electrical communication with the handpiece 600 and, optionally, the second imaging probe 2002. A fixation element 2102 may fix the handpiece relative to the first transmission 610. This structure allows the handpiece to be spaced from, yet still coupled to, the transmission 610. The fixation element 2102 may be a rigid structure providing a firm attachment between the handpiece 600 and the transmission 610.

A second fixation element 2104 may couple the protective sheath 2004 to the second transmission 1702, the second instrument device manipulator 1704, or both. In some embodiments, the second fixation element provides a secure and rigid coupling of the sheath 2004 to the second transmission 1702.

FIG. 22 illustrates coupling a handpiece 600 and an imaging probe 806 to three instrument device manipulators 602. The handpiece 600 and instrument device manipulators 602 may be as substantially described elsewhere herein, such as in relation to FIGS. 2-6C, among others. In the illustrated embodiment, a first instrument device manipulator 602 is coupled to the handpiece 600 by a first transmission 610. The first instrument device manipulator 602 may comprise one or more motors that provide a rotational drive to the treatment probe 616. The treatment probe 616 may be in a fixed linear position with respect to the handpiece 600, and the Z-position of the treatment probe 616 may be operated by positioning the first instrument device manipulator 602. A second instrument device manipulator 1704 may be coupled to a second transmission 1702. The second transmission 1702 may provide a linear translation of an imaging probe 806. The second instrument device manipulator 1704 may additionally support probe functions, such as, for example, aspiration, irrigation, and other plumbing connections, fittings, manifolds, hoses, etc. to allow the second instrument device manipulator 1704 to support instruments provided for these purposes.

A third instrument device manipulator 2202 may be coupled to a third transmission 2204, which in turn, is coupled to a second imaging probe 2002, a second treatment probe 1710, or some other probe. The third instrument device manipulator 2202 may provide for translation and/or rotation of the second imaging probe 2002 or the second treatment probe 1710.

The first, second, and third instrument device manipulators may cooperate to position and actuate the handpiece 600 and its associated instruments.

According to some embodiments, a handpiece 600, which may comprise any of a number of suitable instruments for a wide variety of patient procedures, may be coupled to any of a number of various instrument device manipulators 602 by way of a transmission 610. The motors of the instrument device manipulator 602 may be configured in any arrangement, pattern, spacing, and number of motors. The transmission 610 is configured to couple to the instrument device manipulator 602 and receives, as an input, rotational motion from one or more motors associated with the instrument device manipulator 602. The transmission 610, in turn, is coupled to a handpiece 600 and engages with one or more instruments associated with the handpiece 600 to provide rotational movement, translational movement, or both to one or more instruments associated with the handpiece 600. In some cases, the transmission 610 provides translational motion by translating the entire handpiece 600. In some cases, the instrument device manipulator 602 provides translation of the handpiece 600 by repositioning the instrument device manipulator 602.

The transmission 610 thus performs as an intermediary between any of a variety of instrument device manipulators 602 and any of a variety of handpieces 600. The handpieces 600 do not need to be specifically designed and manufactured to couple to a particular instrument device manipulator 602, as is the case with past systems and methods. Consequently, a handpiece 600 and its concomitant instruments can be designed and manufactured agnostic of the particular instrument device manipulator 602 to which it will be coupled during later use.

Furthermore, the transmission 610 can be reusable for a plurality of procedures. In some embodiments, the handpiece 600 as described herein, may be considered a consumable and may be discarded after each use. In some embodiments, the transmission 610 is incorporated with, or coupled to, a motor pack that provides actuation to the instruments of the handpiece 600, such as for rotation and translation. The transmission 610 may include one or more encoders for sending signals associated with the instruments to a computing device.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Graphic Processing Units (GPUs), Tensor Processing Units (TPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A system of treating or imaging a patient, said system comprising: a probe sized for insertion into the patient; a transmission configured to couple to the probe; and an instrument device manipulator configured to operatively couple to the transmission, the instrument device manipulator comprising one or more motors configured to engage with the transmission; wherein the transmission is configured to receive an input from the one or more motors and is further configured to transmit the input from the one or more motors to the probe to cause the probe to rotate, translate, articulate, or a combination.

Clause 2. The system of clause 1, wherein the probe is a treatment probe, and further comprising an imaging probe sized for insertion into the patient.

Clause 3. The system of clause 2, wherein the imaging probe is a cystoscope.

Clause 4. The system of clause 2, wherein the imaging probe is a TRUS probe.

Clause 5. The system of clause 2, wherein the treatment probe is configured for tissue sample collection.

Clause 6. The system of clause 2, wherein the transmission is configured to receive the input from the one or more motors and cause the treatment probe to rotate, translate, articulate, or a combination.

Clause 7. The system of clause 6, wherein the transmission is configured to receive the input from two or more motors and add the input from the two or more motors to an output of the transmission.

Clause 8. The system of clause 1, wherein the transmission is configured to provide electrical communication between the instrument device manipulator and treatment probe.

Clause 9. The system of clause 8, wherein the electrical communication comprises encoder signals from the treatment probe associated with one or more of position, translation, and rotation of the treatment probe.

Clause 10. The system of clause 8, wherein the electrical communication comprises delivering electrical power to the treatment probe.

Clause 11. The system of clause 1, wherein the transmission comprises a driving gear on a driving shaft and a driven gear on a driven shaft, and wherein the driving shaft and the driven shaft are substantially orthogonal to one another.

Clause 12. The system of clause 11, wherein the driving gear and the driven gear comprise bevel gears.

Clause 13. The system of clause 11, wherein the driving gear and the driven gear comprise spiroid gears.

Clause 14. The system of clause 11, wherein the driving gear and the driven gear comprise worm gears Clause 15. The system of clause 1, wherein the transmission comprises a driving gear or driving pulley on a driving shaft and a driven gear or driven pulley on a driven shaft, and wherein the driving shaft and the driven shaft are substantially parallel to one another.

Clause 16. The system of clause 15, wherein the driving gear and the driven gear comprise spur gears.

Clause 17. The system of clause 15, wherein the driving gear and the driven gear comprise helicoidal gears.

Clause 18. The system of clause 15, wherein the driving pulley and the driven pulley comprise timing pulleys connected by a timing belt.

Clause 19. The system of clause 15, wherein the driving pulley and the driven pulley comprise timing sprockets connected by a timing chain Clause 20. The system of clause 1, wherein the probe further comprises a coupling to releasably couple the probe to the transmission.

Clause 21. The system of clause 20, wherein the coupling is a quick release coupling.

Clause 22. The system of clause 20, wherein the coupling provides a locking engagement.

Clause 23. The system of clause 1, wherein the transmission further comprises a coupling to releasably couple the transmission to the instrument device manipulator.

Clause 24. The system of clause 23, wherein the coupling comprises a quick release coupling.

Clause 25. The system of clause 1, further comprising one or more force sensors operably coupled with the probe and one or more computing devices to detect compression of a tissue of the patient with the probe.

Clause 26. The system of clause 25, wherein the one or more force sensors are operatively coupled to the instrument device manipulator.

Clause 27. The system of clause 1, wherein the transmission is configured to receive the input from one motor of the instrument device manipulator and cause rotational motion of the probe.

Clause 28. The system of clause 1, wherein the transmission is configured to receive input from two or more motors of the instrument device manipulator and cause rotational motion of the probe.

Clause 29. The system of clause 28, wherein the two motors rotate in opposite directions at the same speed.

Clause 30. The system of clause 29, wherein the transmission selectively engages the output from the two motors to the probe.

Clause 31. The system of clause 30, wherein the transmission selectively engages the output from the two motors to the probe in sequence.

Clause 32. The system of clause 31, wherein the transmission is configured to selectively engage one of the two motors to the probe at a time.

Clause 33. The system of clause 30, wherein the transmission further comprises a clutch configured to selectively engage the output from the two motors to the probe.

Clause 34. The system of clause 33, wherein the clutch is a power actuated clutch.

Clause 35. The system of clause 30, wherein the transmission further comprises a torsional shock spring configured to absorb at least some of the torsional stress as the probe is caused to change rotational direction.

Clause 36. The system of clause 30, wherein a first motor of the two motors comprises a first rotary inertia flywheel carried by a first output shaft.

Clause 37. The system of clause 36, wherein a second motor of the two motors comprises a second rotary inertia flywheel carried by a second output shaft.

Clause 38. The system of clause 1, wherein the transmission is a step-down transmission.

Clause 39. The system of clause 1, wherein the transmission is a step-up transmission.

Clause 40. The system of clause 1, wherein the transmission is configured to cause the probe to rotate at a rate of up to 10 revolutions per second.

Clause 41. The system of clause 1, wherein the transmission further comprises a rotary to linear transmission device.

Clause 42. The system of clause 41, wherein the rotary to linear transmission device comprises a rack and pinion system.

Clause 43. The system of clause 41, wherein the rotary to linear transmission device comprises a belt drive.

Clause 44. The system of clause 41, wherein the rotary to linear transmission device comprises a chain drive.

Clause 45. The system of clause 41, wherein the rotary to linear transmission device comprises a lead screw.

Clause 46. The system of clause 41, wherein the rotary to linear transmission device comprises a ball screw.

Clause 47. The system of clause 41, wherein the rotary to linear transmission comprises a roller screw.

Clause 48. The system of clause 1, further comprising an imaging probe.

Clause 49. The system of clause 48, wherein the transmission is configured to receive an input from one of the one or more motors and cause the imaging probe to translate linearly.

Clause 50. The system of clause 1, wherein the instrument device manipulator is a first instrument device manipulator and further comprising a second instrument device manipulator.

Clause 51. The system of clause 50, wherein the first instrument device manipulator is configured to provide movement of the probe, and wherein the second instrument device manipulator is configured to provide movement of an imaging probe.

Clause 52. The system of clause 51, wherein the probe and the imaging probe are carried by a handpiece.

Clause 53. The system of clause 52, wherein the first instrument device manipulator is coupled to the handpiece by a first transmission.

Clause 54. The system of clause 53, wherein the second instrument device manipulator is coupled to the handpiece by a second transmission.

Clause 55. The system of clause 42, wherein one or more of the first transmission and the second transmission is a right-angle shaft transmission.

Clause 56. The system of clause 42, wherein one or more of the first transmission and the second transmission is a parallel shaft transmission.

Clause 57. The system of clause 1, wherein the transmission is operatively coupled to the probe by a shaft coupler.

Clause 58. The system of clause 1, wherein the probe is configured to be coupled to the transmission before the transmission is coupled to the instrument device manipulator.

Clause 59. The system of clause 1, wherein the probe is configured to be coupled to the transmission after inserting the probe into the patient.

Clause 60. The system of clause 1, wherein the probe is positionable in an X direction, a Y direction, a Z direction, or a combination by the instrument device manipulator.

Clause 61. The system of clause 60, wherein the probe is positionable by the instrument device manipulator based at least in part on instructions from a computing device.

Clause 62. The system of clause 60, wherein the probe is positionable by the instrument device manipulator based at least in part on manual manipulation.

Clause 63. The system of clause 62, wherein the instrument device manipulator is manually adjustable to adjust the probe in one or more of at least one rotational axis or at least one translational axis.

Clause 64. The system of clause 1, wherein the transmission further comprises an electrical connector configured to electrically couple the transmission to the instrument device manipulator.

Clause 65. The system of clause 64, wherein the electrical connector is a first electrical connector and the transmission further comprises a second electrical connector configured to electrically couple the transmission to the probe.

Clause 66. The system of clause 65, wherein the transmission is configured to electrically couple the instrument device manipulator with the probe.

Clause 67. The system of clause 1, wherein the probe is a waterjet, and further comprising a pressure regulator configured to dynamically vary water pressure to the waterjet.

Clause 68. A transmission configured to couple a probe to an instrument device manipulator, the transmission comprising: a first coupler to selectively engage with an instrument device manipulator; a second coupler to selectively engage with a probe; a first linkage configured to engage with the instrument device manipulator and receive a motion input from the instrument device manipulator; and a second linkage configured to operatively couple with the probe; wherein the transmission is configured to transfer received motion input from the instrument device manipulator to the probe.

Clause 69. The transmission of clause 68, wherein the probe is a treatment probe, and further comprising an imaging probe coupled to the transmission.

Clause 70. The transmission of clause 69, wherein the motion input is rotational input, and wherein the transmission is configured to receive the rotational input from the instrument device manipulator and cause the treatment probe to rotate, translate, articulate, or a combination.

Clause 71. The transmission of clause 68, wherein the transmission is configured to provide electrical communication between the instrument device manipulator and the probe.

Clause 72. The transmission of clause 68, further comprising an electrical connector to establish electrical communication with the instrument device manipulator when the transmission is coupled to the instrument device manipulator.

Clause 73. The transmission of clause 72, further comprising an electrical signal processor to process position encoding signals providing improved position measurement of the probe.

Clause 74. The transmission of clause 72, further comprising an electrical signal processor to process camera signals from an imaging system arrayed alongside the probe.

Clause 75. The transmission of clause 72, further comprising an electrical signal processor to process position encoding signals providing improved position measurement of a second treatment probe.

Clause 76. The transmission of clause 68, wherein the transmission comprises a driven gear on a driven shaft, and wherein the driven gear is in meshed contact with a driving gear on a driving shaft of the instrument device manipulator.

Clause 77. The transmission of clause 76, wherein the driving shaft and the driven shaft are positioned at substantially right-angles to each other.

Clause 78. The transmission of clause 76, wherein the driving shaft and the driven shaft are substantially parallel to each other.

Clause 79. The transmission of clause 76, wherein the driving gear of the instrument device manipulator provides a rotational motion and the driven gear provides linear translation of the probe.

Clause 80. The transmission of clause 76, wherein the driving gear of the instrument device manipulator provides a rotational motion and the driven gear provides rotational motion of the probe.

Clause 81. The transmission of clause 76, wherein the driving gear of the instrument device manipulator provides a rotational motion and the driven gear provides linear translation of the probe.

Clause 82. The transmission of clause 68, wherein the first coupler is a quick-release coupler.

Clause 83. The transmission of clause 68, wherein the transmission received an input from two motors of the instrument device manipulator, the two motors configured to rotate in opposite directions.

Clause 84. The transmission of clause 83, wherein the transmission transfers the input from the two motors of the instrument device manipulator to the probe to oscillate the probe about a longitudinal axis of the probe a predetermined number of degrees.

Clause 85. The transmission of clause 84, wherein the transmission is configured to selectively engage and disengage the two motors with the probe.

Clause 86. The transmission of clause 85, further comprising a clutch mechanism, the clutch mechanism operable to selective engage and disengage the two motors with the probe.

Clause 87. The transmission of clause 86, wherein the clutch mechanism is electrically actuatable.

Clause 88. The transmission of clause 84, wherein the transmission transfers the input from the two motors of the instrument device manipulator to the probe in response to an instruction from a computing device.

Clause 89. The transmission of clause 68, wherein the probe is an imaging probe and the transmission is configured to transfer received motion input from the instrument device manipulator to linear motion of the imaging probe.

Clause 90. The transmission of clause 68, wherein the transmission is configured to receive two or more inputs from the instrument device manipulator.

Clause 91. The transmission of clause 90, wherein the transmission is configured to receive the two or more inputs and combine the two or more inputs into a single output.

Clause 92. The transmission of clause 90, wherein the transmission is configured to receive five or more inputs from the instrument device manipulator.

Clause 93. The transmission of clause 74 or 75, wherein the inputs from the instrument device manipulator comprise rotational inputs.

Clause 94. The transmission of clause 93, wherein individual ones of the rotational inputs comprise a gear coupled to a motor.

Clause 95. A transmission, comprising: a first coupling configured to operably couple to a probe; a second coupling configured to operably couple to an instrument device manipulator; and an electrical system interface configured to provide electrical communication between the probe and the instrument device manipulator.

Clause 96. The transmission of clause 95, wherein the transmission is configured to transfer input motion from the instrument device manipulator to motion of the probe.

Clause 97. The transmission of clause 96, wherein the input motion is rotational motion and the motion of the probe is rotational motion.

Clause 98. The transmission of clause 96, wherein the input motion is rotational motion and the motion of the probe is linear motion.

Clause 99. A system of treating or imaging a patient, said system comprising: a probe sized for insertion into the patient; and an instrument device manipulator configured to operatively couple to the probe, the instrument device manipulator comprising one or more motors configured to engage with the probe; wherein the probe is configured to receive an input from the one or more motors and is further configured to transmit the rotational input from the one or more motors to the probe to cause the probe to rotate, translate, articulate, or a combination.

Clause 100. The system of clause 99, further comprising a transmission coupled between the probe and the instrument device manipulator, the transmission configured to transmit an output of the one or more motors to the probe.

Clause 101. The system of any one of the preceding clauses, wherein the probe is configured to provide energy for hemostasis of treated tissue.

Clause 102. The system of clause 101, wherein the energy for hemostasis is applied without concurrent image guidance.

Clause 103. The system of any one of the preceding clauses, wherein the probe is configured to treat or remove a kidney stone.

Clause 104. The system of any one of the preceding clauses, wherein the probe is configured to treat or remove cancer.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system of treating a patient, said system comprising:
   a treatment probe sized for insertion into the patient, the treatment probe comprising an energy source configured to deliver energy to the tissue to treat the patient;
   a transmission configured to selectively couple to the treatment probe, the transmission comprising a housing and one or more inputs and an output shaft;
   an instrument device manipulator configured to operatively couple to the transmission, the instrument device manipulator comprising one or more motors in driving engagement with one or more outputs through one or more clutches, the one or more outputs configured to engage with the one or more inputs of the transmission; and
   wherein a first motor of one or more motors is couplable to a first of the one or more outputs through a first of the one or more clutches to cause the energy source of the treatment probe to rotate in a first direction about an axis and a second motor of the one or more motors is couplable to a second of the one or more outputs through a second of the one or more clutches to rotate the energy source of the treatment probe in a second direction about the axis, opposite the first direction, the instrument device manipulator configured to selectively switch between the first motor and the second motor with the first clutch and the second clutch to selectively rotate the energy source of the treatment probe in the first direction or the second direction about the axis, and
   wherein the output shaft and the one or more inputs extend through the housing.

2. The system of claim 1, further comprising an imaging probe sized for insertion into the patient.

3. The system of claim 2, wherein the imaging probe is a cystoscope.

4. The system of claim 2, wherein the imaging probe is a transrectal ultrasonic probe.

5. The system of claim 2, wherein the treatment probe is configured for tissue sample collection.

6. The system of claim 1, wherein the transmission is configured to receive an input from a first motor of the one or more motors as a first input and a second motor of the one or more motors as a second input and combine the first input and the second input to a single transmission output.

7. The system of claim 1, wherein the transmission is configured to provide electrical communication between the instrument device manipulator and the treatment probe.

8. The system of claim 7, wherein the electrical communication comprises encoder signals from the treatment probe associated with one or more of position, translation, and rotation of the treatment probe.

9. The system of claim 7, wherein the electrical communication comprises delivering electrical power to the treatment probe.

10. The system of claim 1, wherein the transmission comprises a driving gear on a driving shaft and a driven gear on a driven shaft, and wherein the driving shaft and the driven shaft are substantially orthogonal to one another.

11. The system of claim 10, wherein the driving gear and the driven gear comprise bevel gears.

12. The system of claim 10, wherein the driving gear and the driven gear comprise helicoid gears.

13. The system of claim 10, wherein the driving gear and the driven gear comprise worm gears.

14. The system of claim 1, wherein the transmission comprises a driving gear or a driving pulley on a driving shaft and a driven gear or a driven pulley on a driven shaft, and wherein the driving shaft and the driven shaft are substantially parallel to one another.

15. The system of claim 14, wherein the driving gear and the driven gear comprise spur gears.

16. The system of claim 14, wherein the driving gear and the driven gear comprise helicoidal gears.

17. The system of claim 14, wherein the driving pulley and the driven pulley comprise timing pulleys connected by a timing belt.

18. The system of claim 14, wherein the driving pulley and the driven pulley comprise timing sprockets connected by a timing chain.

19. The system of claim 1, wherein the treatment probe further comprises a second coupling to releasably couple the treatment probe to the transmission.

20. The system of claim 1, wherein the instrument device manipulator further comprises:
   a third motor of the one or more motors coupled to the transmission and configured to translate the treatment probe.

21. The system of claim 1, wherein a processor is operatively coupled to the transmission to rotate the energy source in the first direction or the second direction and configured to control the rotational speed of the energy source and clutch timing in accordance with a treatment plan.

* * * * *